(12) United States Patent
Cai et al.

(10) Patent No.: US 6,201,016 B1
(45) Date of Patent: Mar. 13, 2001

(54) COMPOUNDS AND METHODS FOR THE TREATMENT OF CARDIOVASCULAR, INFLAMMATORY AND IMMUNE DISORDERS

(75) Inventors: Xiong Cai, Framingham; Gurmit Grewal, Natick; Sajjat Hussoin, Lexington; Aberra Fura, Cambridge; Ralph Scannell, Hopkinton, all of MA (US); Tesfaye Biftu, Westfield, NJ (US)

(73) Assignee: CytoMed Incorporated, Cambridge, MA (US)

( * ) Notice: Subject to any disclaimer, the term of this patent is extended or adjusted under 35 U.S.C. 154(b) by 0 days.

(21) Appl. No.: 08/390,641

(22) Filed: Feb. 17, 1995

Related U.S. Application Data

(63) Continuation-in-part of application No. 08/265,656, filed on Jun. 27, 1994, now Pat. No. 5,792,776.

(51) Int. Cl.$^7$ .......................... A61K 31/34; A61K 31/38; A61K 31/44; A61K 31/17
(52) U.S. Cl. .......................... 514/471; 514/438; 514/303; 514/428; 514/588; 549/491; 549/77; 546/118; 548/567; 564/47
(58) Field of Search .................................. 549/480, 487, 549/49, 177; 514/472, 471, 438, 303, 428, 588; 546/118; 548/567; 564/47

(56) References Cited

U.S. PATENT DOCUMENTS

| | | | |
|---|---|---|---|
| 5,047,420 | 9/1991 | Graham et al. | 514/484 |
| 5,344,843 | 9/1994 | Guthrie et al. | 549/71 |
| 5,463,083 | 10/1995 | Biftu et al. | 514/473 |

FOREIGN PATENT DOCUMENTS

| | | |
|---|---|---|
| 464924 | 12/1968 | (CH) . |
| 0 257 921 | 3/1988 | (EP) . |
| 0 465 122 A1 | 1/1992 | (EP) . |
| 2 263 109 | 7/1993 | (GB) . |
| WO 89/04299 | 5/1989 | (WO) . |
| WO 91/17157 | 11/1991 | (WO) . |
| 92 13848 * | 8/1992 | (WO) . |
| WO 93/01191 | 1/1993 | (WO) . |
| WO 93/16075 | 8/1993 | (WO) . |
| WO 95/18610 | 7/1995 | (WO) . |
| WO 96/00212 | 1/1996 | (WO) . |

OTHER PUBLICATIONS

Communication dated Mar. 4, 1997 in European Patent Appl. No. 95907972.4.

* cited by examiner

*Primary Examiner*—Deborah C. Lambkin
(74) *Attorney, Agent, or Firm*—Hale and Dorr LLP

(57) ABSTRACT

Enantiomerically enriched disubstituted tetrahydrofurans, tetrahydrothiophenes, pyrrolidines and cyclopentanes are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

It has been determined that 5-lipoxygenase activity, oral availability, and stability in vivo (for example, glucuronidation rate) can vary significantly among the optical isomers of the disclosed compounds.

15 Claims, 4 Drawing Sheets

COMPOUNDS AND METHODS FOR THE TREATMENT OF CARDIOVASCULAR, INFLAMMATORY AND IMMUNE DISORDERS

This application is a continuation-in-part of U.S. Ser. No. 08/265,656, filed on Jun. 27, 1994, U.S. Pat. No. 5,792,776.

FIELD OF THE INVENTION

This invention is in the area of 2,5-disubstituted tetrahydrothiophenes, tetrahydrofurans, pyrrolidines and 1,3-disubstituted cyclopentanes. The compounds exhibit biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

BACKGROUND OF THE INVENTION

Platelet activating factor (PAF, 1-o-alkyl-2-acetyl-sn-glycerol-3-phosphorylcholine) is a potent inflammatory phospholipid mediator with a wide variety of biological activities. PAF was initially identified as a water soluble compound released by immunoglobulin E (IgE)-sensitized rabbit basophils. It is now known that PAF is also generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. (Hwang, "Specific receptors of platelet-activating factor, receptor heterogeneity, and signal transduction mechanisms", *Journal of Lipid Mediators* 2, 123 (1990)). PAF causes the aggregation and degranulation of platelets at very low concentrations. The potency (active at $10^{-12}$ to $10^{-9}$ M), tissue level (picomoles) and short plasma half life (2–4 minutes) of PAF are similar to those of other lipid mediators such as thromboxane A, prostaglandins, and leukotrienes.

PAF mediates biological responses by binding to specific PAF receptors found in a wide variety of cells and tissues. Structure-activity studies on PAF and its analogs indicate that the ability of PAF to bind to these receptors is structure specific and stereospecific. (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states.

The involvement of PAF in pathological inflammatory and immune states has stimulated a substantial research effort to identify PAF receptor antagonists. In 1983, a phospholipid analog referred to as CV-3988 (rac-3-(N-n-octadecyl-carbamoyloxy-ω-methoxypropyl-2-thiazolioethyl phosphate) was reported to have PAF receptor antagonist properties. (Terashita, et al., *Life Sciences* 32, 1975 (1983).) In other early work in this area, Shen, et al., (in *Proc. Natl. Acad. Sci. (U.S.A.)* 82, 672 (1985)), reported that kadsurenone, a neolignan derivative isolated from Piper futokadsura Sieb et Zucc (a Chinese herbal plant) was a potent, specific and competitive inhibitor of PAF activity at the receptor level.

Hwang, et al., disclosed in 1985 that trans-2,5-bis-(3,4,5-trimethoxyphenyl) tetrahydrofuran (L-652,731) inhibits the l- binding of tritiated PAF to PAF receptor sites. (Hwang, et al., "Trans-2, 5-bis-(3,4,5-trimethoxyphenyl) tetrahydrofuran", *Journal of Biological Chemistry* 260, 15639 (1985).) L-652,731 was found to be orally active, and to inhibit PAF-induced rat cutaneous vascular permeability at a dosage of 30 aglkg body weight. The compound was found to have no effect on the enzyme 5-lipoxygenase. Hwang, et al. also reported that trans-L-652,731 (wherein the aryl groups at the 2 and 5 positions are on opposite sides of the plane of the tetrahydrofuran ring) is approximately 1000 times more potent than cis-L-652,731 (wherein the 2 and 5 aryl substituents are on the same side of the plane of the tetrahydrofuran ring).

In 1988, Hwang, et al., reported that L-659,989 (trans-2-(3-methoxy-4-propoxyphenyl-5-methylsulfonyl)-5-(3,4,5-trimethoxyphenyl)tetrahydrofuran) is an orally active, potent, competitive PAF receptor antagonist, with an equilibrium inhibition constant 10 times greater than that of trans-L-652,731. (Hwang, et al., *J. Pharmacol. Ther.* 246, 534 (1988).)

U.S. Pat. Nos. 4,996,203, 5,001,123 and 4,539,332 to Biftu, et al. and European Patent Application Nos. 89202593.3, 90306235.4, and 90306234.7 disclose that specific classes of 2,5-diaryl tetrahydrofurans are PAF receptor antagonists.

Bowles et al., *Synlett*, 1993, pp 111 disclose a limited number of substituted tetrahydrofurans which may possess PAF receptor antagonism.

Danyoshi et al., *Chem. Pharm. Bull.*, 1989, pp 1969, disclose 2-substituted-N-alkoxycarbonyl pyrrolidines which inhibit PAF induced rabbit platelet aggregation.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxyeicosatetraenoic acid (5-HPETE), that is converted to leukotriene A4, that in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a research effort to develop specific receptor antagonists or inhibitors of leukotriene biosynthesis, to prevent or minimize pathogenic inflammatory responses mediated by these compounds.

Leukotrienes are released simultaneously from leukocytes with PAF, possibly from a common phospholipid precursor such as 1-O-hexadecyl-2-arachidonyl-sn-glycero-phosphocholine, and upon cellular activation, act synergistically with PAF in many biological models. European Patent Application Nos. 90117171.0 and 901170171.0 disclose indole, benzofuran, and benzothiophene lipoxygenase inhibiting compounds.

Recently, it was reported that the tetrahydrothiophene derivative of L-652,731, trans-2,5-bis-(3,4,5-trimethoxyphenyl)tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors. (Biftu, et al., *Abstr. of 6$^{th}$Int. Conf. on*

*Prostaglandins and Related Compounds,* Jun. 3–6, 1986, Florence, Italy; U.S. Pat. No. 4,757,084 to Biftu); WO 92/15294; WO 94/01430; WO 94/04537; and WO 94/06790.

WO 92/13848 discloses a class of racemic lipoxygenase-inhibiting hydroxamic acid and N-hydroxyurea derivatives of the structure

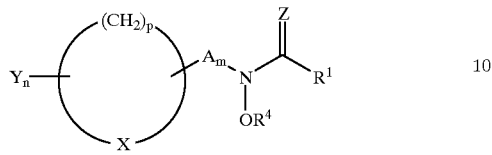

wherein $R^1$ is hydrogen, alkyl, alkenyl, amino or substituted amino, $R^4$ is hydrogen, a pharmaceutically acceptable cation, aroyl or alkoyl, A is alkylene or alkenylene, X is oxygen or sulfur, each Y is hydrogen, halo, cyano, hydroxy, alkyl, alkoxy, alkylthio, alkenyl, alkoxyalkyl, cycloalkyl, aryl, aryloxy, arylalkyl, arylalkenyl, arylalkoxy or substituted aryl, Z is oxygen or sulfur, m is 0 or 1, n is 1 to 5 and p is 2 to 6, inhibit the enzyme lipoxygenase.

Given the significant number of pathological immune and inflammatory responses that are mediated by PAF and leukotrienes, there remains a need to identify new compounds and compositions that exhibit PAF receptor antagonistic activity or inhibit the enzyme 5-lipoxygenase.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions for the treatment of pathological immune or inflammatory disorders mediated by PAF or products of 5-lipoxygenase.

It is another object of the present invention to provide a method for the treatment of pathological immune or inflammatory disorders mediated by PAF or products of 5-lipoxygenase.

SUMMARY OF THE INVENTION

Compounds of Formula I are provided

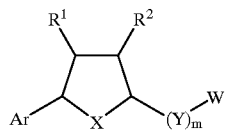

(I)

wherein:
Ar is an aryl or heteroaryl group that is optionally substituted, preferably with halo (including but not limited to fluoro), lower alkoxy (including methoxy), lower aryloxy (including phenoxy), W, cyano, or $R^3$; m is 0 or 1;

W is independently —AN(OM)C(O)N($R^3$)$R^4$, —AN($R^3$)C(O)N(OM)$R^4$, —AN(OM)C(o)$R^4$, —AC(O)N(OM)$R^4$, —C(o)N(OM)$R^4$, —C(O)NHA, or —A—B;

A is lower alkyl, lower alkenyl, lower alkynyl, alkaryl or aralkyl groups, wherein one or more carbons optionally can be replaced by O, N, or S, however, —Y—A— should not include two adjacent heteroatoms (i.e., —O—O—, —S—S—, —O—S—, etc.);

B is selected from the group consisting of pyridylimidazole and benzimidazole, either of which is optionally substituted with $R_3$, and wherein the pyridylimidazole or benzimidazole is preferably connected to A through a nitrogen atom;

M is hydrogen, a pharmaceutically acceptable cation, or a metabolically cleavable leaving group;

X is O, S, S(O), NRC, or $CHR^5$;

an Y is O, S, S(O), NRW, or $CHR^5$;

$R^1$ and $R^2$ are independently hydrogen, lower alkyl including methyl, cyclopropylmethyl, ethyl, isopropyl, butyl, pentyl hexyl, and Cal cycloalkyl, for example, cyclopentyl; halo lower alkyl, for example, trifluoromethyl; halo, for example fluoro; and —COOH;

$R^1$ and $R^4$ are independently hydrogen or alkyl, alkenyl, alkynyl, aryl, aralkyl, alkaryl, $C_{1-6}$ alkoxy-$C_{1-10}$ alkyl, $C_1$-alkylthio-$C_{1-10}$ alkyl, heteroaryl, or heteroarylalkyl-;

$R^5$ is hydrogen, lower alkyl, lower alkenyl, lower alkynyl, alkaryl, —AN(OM)C(O)N($R^3$)$R^4$, —AN($R^3$)C(O)N(OM)$R^4$, —AN(OM)C(O)$R^4$, —AC(O)N(OM)$R^4$, —AC(O)N(ON)$R^4$, —AS(O)n$R^3$, —AS(O)$_n$CH$_2$C(O)$R^3$, —AS(O)$_n$CH$_2$CH(OH)$R^3$, —AC(O)NHR$^3$; and wherein n is 0–2.

The Ar group, in one embodiment, is selected from the group consisting of phenyl, trimethoxyphenyl, dimethoxyphenyl, fluorophenyl, and specifically 4-fluorophenyl, difluorophenyl, pyridyl, dimethoxypyridyl, quinolinyl, furyl, imidazolyl, and thienyl groups.

In one embodiment, —A—B is

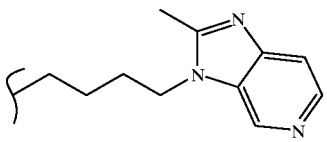

and Ar is an optionally substituted aryl or heteroaryl group, as described in more detail in section I.A. below.

Nonlimiting examples of preferred compounds are:

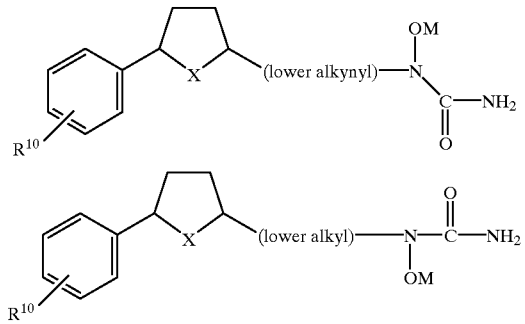

wherein $R^{10}$ is halogen, —CN, hydrogen, lower alkyl, lower alkenyl, lower alkynyl, or [name others of interest].

These compounds in general reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i. e., by acting as both a PAF receptor antagonist and inhibitor of 5-lipoxygenase.

Another embodiment of the present invention is a pharmaceutical composition that includes an effective amount of a compound of Formula I or its pharmaceutically acceptable salt or derivative in combination with a pharmaceutically acceptable carrier.

A method to treat disorders mediated by PAF or leukotrienes is also disclosed, that includes administering an effective amount of one or more of the above-identified compounds or a pharmaceutically acceptable salt or derivative thereof, optionally in a pharmaceutically acceptable carrier.

It has been surprisingly determined that 5-lipoxygenase activity, oral availability, and stability in vivo (for example, glucuronidation rate) can vary significantly among the optical isomers of the disclosed compounds. Therefore, in one embodiment of the invention, the compound is administered in an enantiomerically enriched form, i.e., substantially in the form of one isomer.

Examples of immune, allergic and cardiovascular disorders include general inflammation, cardiovascular disorders including hypertension, skeletal-muscular disorders, osteoarthritis, gout, asthma, lung edema, adult respiratory distress syndrome, pain, aggregation of platelets, shock, rheumatoid arthritis, juvenile rheumatoid arthritis, psoriatic arthritis, psoriasis, autoimmune uveitis, allergic encephalomyelitis, systemic lupus erythematosis, acute necrotizing hemorrhagic encephalopathy, idiopathic thrombocytopenia, polychondritis, chronic active co hepatitis, idiopathic sprue, Crohn's disease, Graves ophthalmopathy, primary biliary cirrhosis, uveitis posterior, interstitial lung fibrosis; allergic asthma; and inappropriate allergic responses to environmental stimuli such as poison ivy, pollen, insect stings and certain foods, including atopic dermatitis and contact dermatitis.

The compounds disclosed herein can also be used as research tools to study the structure and location of PAF receptors as well as biological pathways involving leukotrienes.

The following are nonlimiting examples of compounds that fall within Formula I. These examples are merely exemplary, and are not intended to limit the scope of the invention:

2-(3,4,5-trimethoxyphenyl)-5-[3-(N'-methyl-N'-hydroxyureidyl)propoxy] tetrahydrofuran;
2-(4-fluorophenyl)-5-[3-(N'-methyl-N'-hydroXyureidyl) propoxy] tetrahydrofuran;
2-(3,4,5-trimethoxyphenyl)-5-[3- (N'-n-butyl-N'-hydroxyureidyl)-propoxy)tetrahydrofuran;
2-(4-fluorophenyl)-5-[3-(N'-n-butyl-N'-hydroxyureidyl) propoxy] tetrahydrofuran;
2-(3',4-dimethoxyphenyl)-5-[3-(N-butyl-N-hydroxyureidyl)]-propoxytetrahydrofuran;
2-(3',4'-dimethoxyphenyl)-5-[3-(N-methyl-N-hydroxyureidyl)-propoxytetrahydrofuran;
2-(2,4,5-trimethoxyphenyl) -5-(3-hydroxyureidylpropoxy) -tetrahydrofuran;
2-(4-fluorophenyl)-5-(3-hydroxyureidylpropoxy) tetrahydrofuran;
2-(4-fluorophenyl)-5-[3-(N'-methyl-N'-hydroxyureidyl) propoxy]tetrahydrothiophene; and
2-(4-fluorophenyl)-5-(3-hydroxyureidylpropoxy) tetrahydrothiophene.

Further nonlimiting examples of other compounds that fall within Formula I are set forth below in Tables 1 and 2 and FIGS. 1a and 1b.

TABLE 1

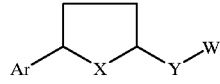

| Ar | X* | W |
|---|---|---|
| 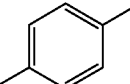 | O | CH$_2$CH$_2$CH$_2$NHC(O)N(OH)CH$_3$ |
| SAME | C | SAME |
| SAME | S | SAME |
| SAME | NH | SAME |
| SAME | O | CH$_2$CH$_2$CH$_2$N(OH)C(O)NH$_2$ |
| SAME | C | SAME |
| SAME | S | SAME |
| SAME | NH | SAME |
| SAME | O | CH$_2$CH$_2$CH$_2$N(OH)C(O)NHCH$_3$ |
| SAME | C | SAME |
| 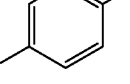 | O | CH$_2$—CH=CH—CH$_2$N(OH)CONH$_2$ |
| 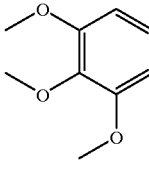 | SAME AS ABOVE | SAME AS ABOVE |
| 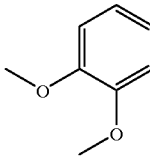 | SAME AS ABOVE | SAME AS ABOVE |
| 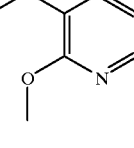 | SAME AS ABOVE | SAME AS ABOVE |
| 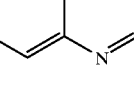 | SAME AS ABOVE | SAME AS ABOVE |

*C refers to CHR$^5$. Y is O, CHR$^5$, S, or NH.

TABLE 2

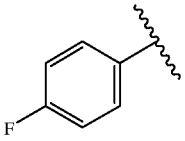

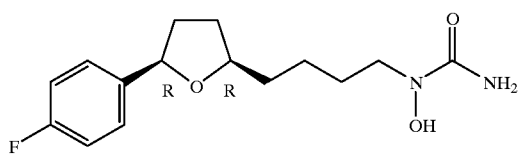

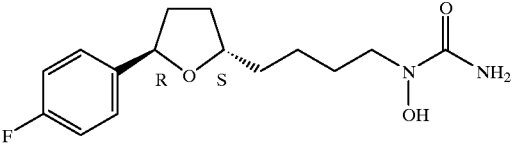

DETAILED DESCRIPTION OF THE INVENTION

Figure 1A:
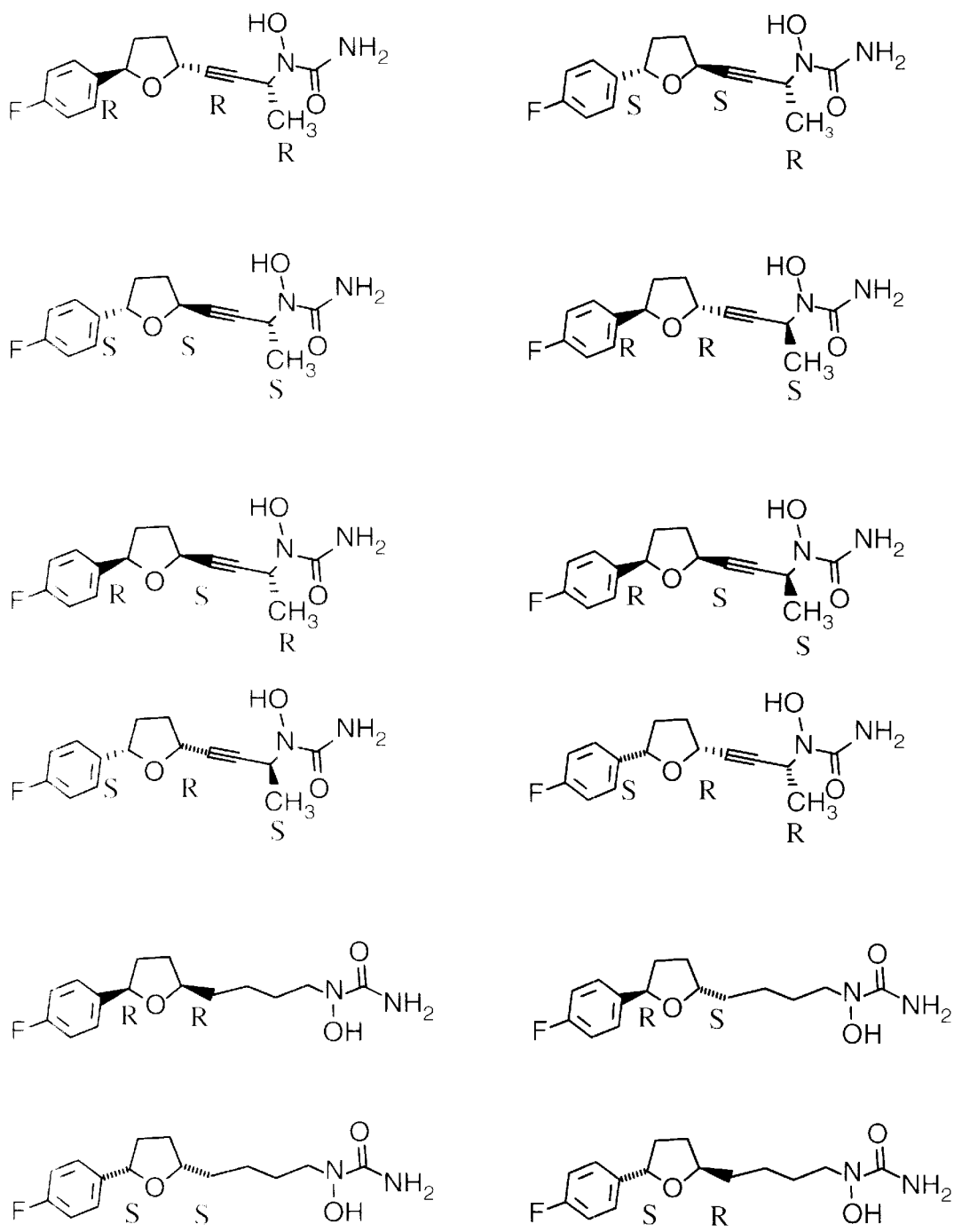
FIGS. 1a and 1b are illustrations of the chemical structures with indicated stereochemistry of selected active compounds.
Figure 1B:
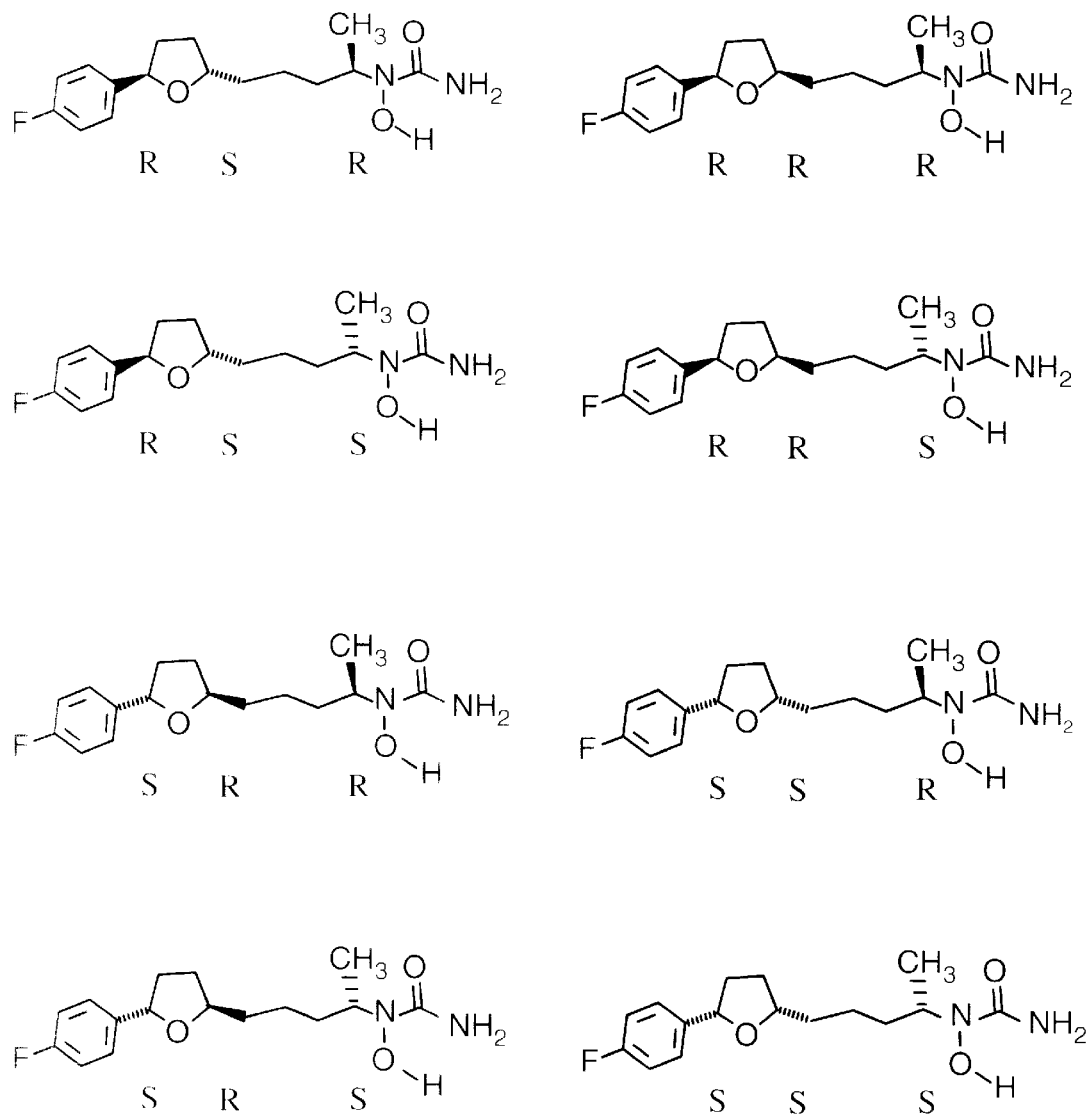

1. Description and Synthesis of the Compounds

A. Compounds As used herein, the term "enantiomerically enriched" refers to a compound in the form of at least approximately 95%, and preferably approximately 97%, 98%, 99%, or 100% of a single enantiomer of that compound.

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to $R^3$ or one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either[] unprotected, or protected, as necessary, as known to those skilled in the art, for example, as taught in Greene, et al., "Protective Groups in Organic Synthesis," John Wiley and Sons, Second Edition, 1991.

The term halo, as used herein, refers to chloro, fluoro, iodo, or bromo.

The term lower alkyl, as used herein, and unless otherwise specified, refers to a $C_1$ to $C_6$ saturated straight, branched, or cyclic (in the case of C>) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl, optionally substituted as described above for the alkyl groups.

The term alkenyl, as referred to herein, and unless otherwise specified, refers to a straight, branched, or cyclic (in the case of $C_{5-6}$) hydrocarbon of $C_1$ to $C_{10}$ with at least one double bond, optionally substituted as described above.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond, optionally substituted as described above. The term lower alkynyl, as referred to herein, and unless otherwise specified, refers to a $C_2$ to $C_6$ alkynyl group, specifically including acetylenyl, propynyl, and —C*C—CH(alkyl)—, including —C*C—CH(CH$_3$)—.

The term aryl, as used herein, and unless otherwise specified, refers to phenyl, biphenyl, or napthyl, and preferably phenyl. The aryl group can be optionally substituted with any suitable group, including but not limited to one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, and preferably with halo (including but not limited to fluoro), lower alkoxy (including methoxy), lower aryloxy (including phenoxy), W, cyano, or $R^3$.

The term haloalkyl, haloalkenyl, or haloalkynyl refers to a alkyl, alkenyl, or alkynyl group in which at least one of the hydrogens in the group has been replaced with a halogen atom.

The term heteroaryl, heterocycle or heteroaromatic, as used herein, refers to an aromatic moiety that includes at least one sulfur, oxygen, or nitrogen in the aromatic ring, which can optionally be substituted as described above for the aryl groups. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term aralkyl refers to an aryl group with an alkyl substituent.

The term alkaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic -moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term PAF receptor antagonist refers to a compound that binds to a PAF receptor with a binding constant of 30 $\mu$M or lower.

The term 5-lipoxygenase inhibitor refers to a compound that inhibits the enzyme at 30 $\mu$M or lower in a broken cell system.

The term pharmaceutically active derivative refers to any compound that upon administration to the recipient, is capable of providing directly or indirectly, the compounds disclosed herein.

The 2,5-disubstituted tetrahydrothiophenes, tetrahydrofurans and pyrrolidines, as well as the 1,3-disubstituted.cyclopentanes described herein exhibit PAF receptor antagonist activity or inhibit the enzyme 5-lipoxygenase, or have dual activity, and are thus useful in the treatment of humans who have immune allergic or cardiovascular disorders that are mediated by PAF or products of 5-lipoxygenase.

B. stereochemistry

It has been surprisingly determined that 5-lipoxygenase activity, oral availability, and stability in vivo (for example, glucuronidation rate) can vary significantly among the optical isomers of the disclosed compounds. Therefore, in a preferred embodiment, the active compound or its precursor is administered in an enantiomerically enriched form, i.e., substantially in the form of one isomer. The preferred enantiomer is easily determined by evaluating the various possible enantiomers in selected biological assays, for example, those described in detail herein.

The 2,5-disubstituted tetrahydrofurans, tetrahydrothiophenes, and pyrrolidines exhibit a number of stereochemical configurations. Carbon atoms 2 and 5 in the center ring are chiral, and thus the center ring exists at a minimum as a diastereomeric pair. Each diastereomer exists as a set of enantiomers. Therefore, based on the chiral $C_2$ and $C_5$ atoms alone, the compound is a mixture of four enantiomers.

If non-hydrogen substituents are located on carbon atoms 3 and 4 in the center ring, then the $C_3$ and $C_4$ atoms are also chiral, and can also exist as a diastereomeric pair, that is also a mixture of four enantiomers.

The 1,3-cyclopentanes disclosed herein also exhibit a number of stereochemical configurations. Carbon atoms 1 and 3 in the center ring are chiral, and thus the center ring exists at a minimum as a diastereomeric pair. Each diastereomer exists as a set of enantiomers. Therefore, based on the chiral $C_1$ and $C_3$ atoms alone, the compound is a mixture of four enantiomers.

If non-hydrogen substituents are located on carbon atoms 4 and 5 in the center ring, then the $C_4$ and $C_5$ atoms are also chiral, and can also exist as a diastereomeric pair, that is also a mixture of four enantiomers.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. For example, if the compound is basic, one can use chiral acids that form diastereomeric derivatives that may possess significantly different solubility properties. Non-limiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of a free hydroxyl group with a chiral acid also results in the formation of diastereomeric derivatives whose physical properties may differ sufficiently to permit separation.

Enantiomerically pure or enriched compounds can be obtained by passing the racemic mixture through a chromatographic column that has been designed for chiral separations, or by enzymatic resolution of appropriately modified substrates.

C. Syntheses of Active Compounds

The 2,5-disubstituted tetrahydrofurans, tetrahydrothiophenes, and pyrrolidines disclosed herein can be prepared in a variety of ways known to those skilled in the art, including by methods disclosed by Whittaker et al, Synlett, 1993 pp 111, Biorg. Med. Lett., 1993 pp 1499; Achiwa et al., Chem. Pharm. Bull., 1989, pp. 1969. These compounds can be prepared in both racemic and entantiomerically enriched forms.

For example, one method for the synthesis of entantiomerically enriched materials is set forth below in Scheme 1. In this method, the enantiomeric synthesis begins with the chiral reduction of a ketone. After ring closure and reaction of the —OH group, the cis and trans isomers can be separated by standard means known to those skilled in the art, affecting a diastereomeric resolution. Additional chiral centers can be resolved using techniques known to those skilled in the art, including those set forth in the examples below.

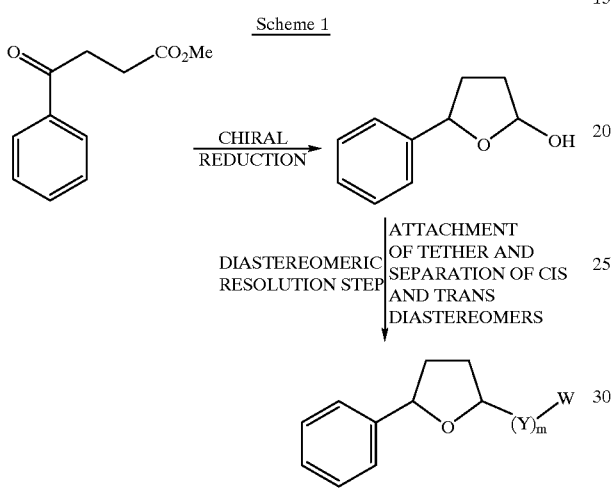

1,3-Disubstituted cyclopentanes can be prepared using the procedure of Graham, et al. (1,3-Diaryl Cyclopentanes: A New Class of Potent PAF Receptor Antagonists. 197th ACS National Meeting, Dallas, Tex., Apr. 9–14, 1989, Division of Medicinal Chemistry, poster no. 25 (abstract)), or by other known methods.

A general procedure for preparing a hydroxyurea is shown below in Scheme 2:

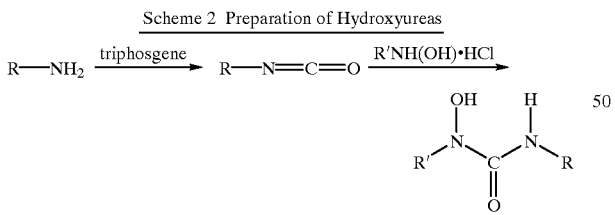

General procedures for preparing reverse hydroxyureas are a shown in Scheme 3:

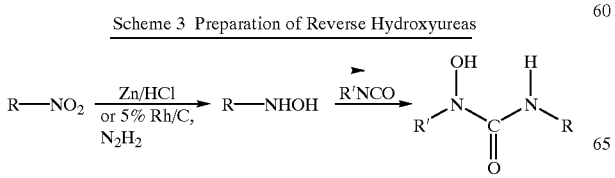

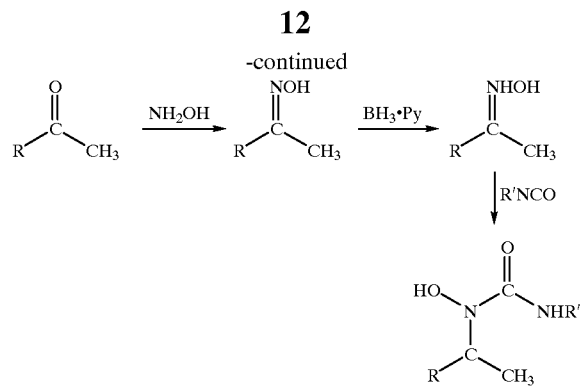

A general procedure for preparing a hydroxamic acid is shown in Scheme 4:

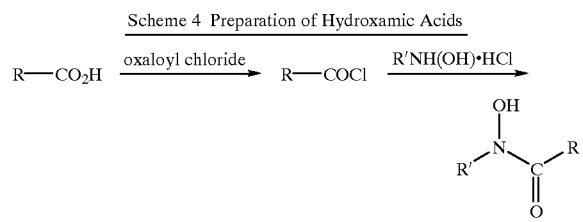

A general procedure for preparing a reverse hydroxamic acid is shown in Scheme 5:

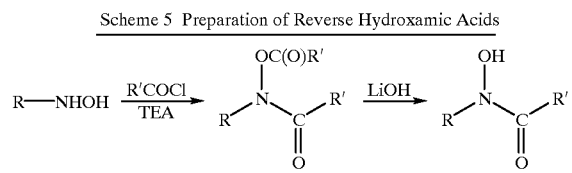

Scheme 6 shows the synthesis of 2-(3,4,5-trimethoxyphenyl)-5-[3-(N'-substituted-N'-hydroxyureidyl) propoxy] tetrahydrofuran (1-4) and 2-(4-fluorophenyl)-5-[3-(N'-substituted-N'-hydroxyureidyl) propoxy) tetrahydrofuran (9–12):

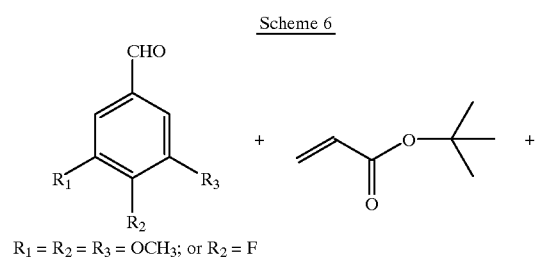

$R_1 = R_2 = R_3 = OCH_3$; or $R_2 = F$

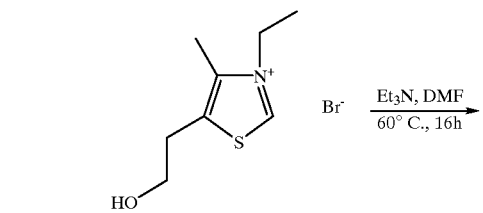

-continued

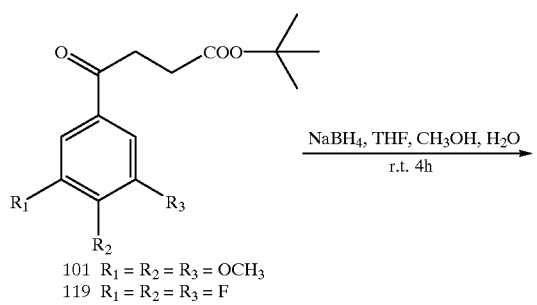

101 R₁ = R₂ = R₃ = OCH₃
119 R₁ = R₂ = R₃ = F

NaBH₄, THF, CH₃OH, H₂O
r.t. 4h
→

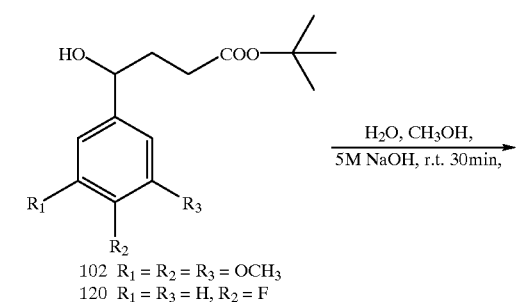

102 R₁ = R₂ = R₃ = OCH₃
120 R₁ = R₃ = H, R₂ = F

H₂O, CH₃OH,
5M NaOH, r.t. 30min,
→

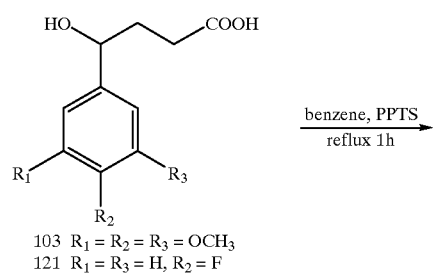

103 R₁ = R₂ = R₃ = OCH₃
121 R₁ = R₃ = H, R₂ = F benzene, PPTS
reflux 1h
→

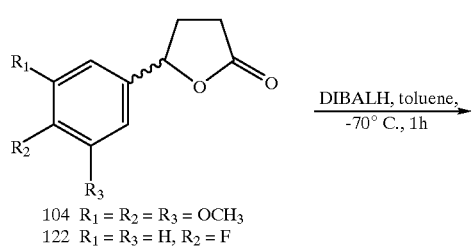

104 R₁ = R₂ = R₃ = OCH₃
122 R₁ = R₃ = H, R₂ = F

DIBALH, toluene,
-70° C., 1h
→

-continued

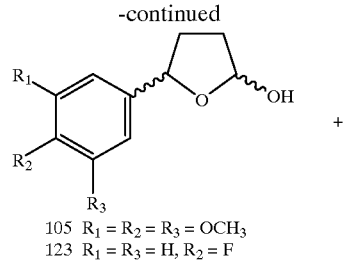

105 R₁ = R₂ = R₃ = OCH₃
123 R₁ = R₃ = H, R₂ = F

+

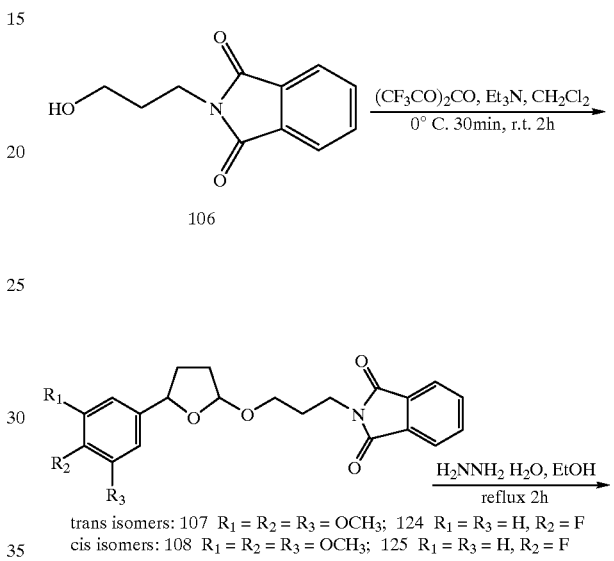

106

(CF₃CO)₂CO, Et₃N, CH₂Cl₂
0° C. 30min, r.t. 2h
→ trans isomers: 107 R₁ = R₂ = R₃ = OCH₃; 124 R₁ = R₃ = H, R₂ = F
cis isomers: 108 R₁ = R₂ = R₃ = OCH₃; 125 R₁ = R₃ = H, R₂ = F H₂NNH₂ H₂O, EtOH
reflux 2h
→

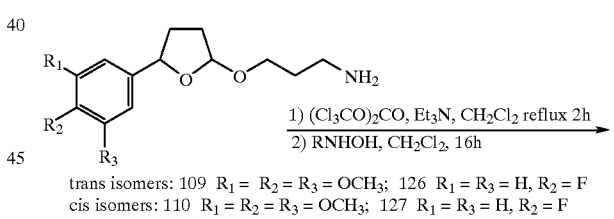

1) (Cl₃CO)₂CO, Et₃N, CH₂Cl₂ reflux 2h
2) RNHOH, CH₂Cl₂, 16h
→ trans isomers: 109 R₁ = R₂ = R₃ = OCH₃; 126 R₁ = R₃ = H, R₂ = F
cis isomers: 110 R₁ = R₂ = R₃ = OCH₃; 127 R₁ = R₃ = H, R₂ = F

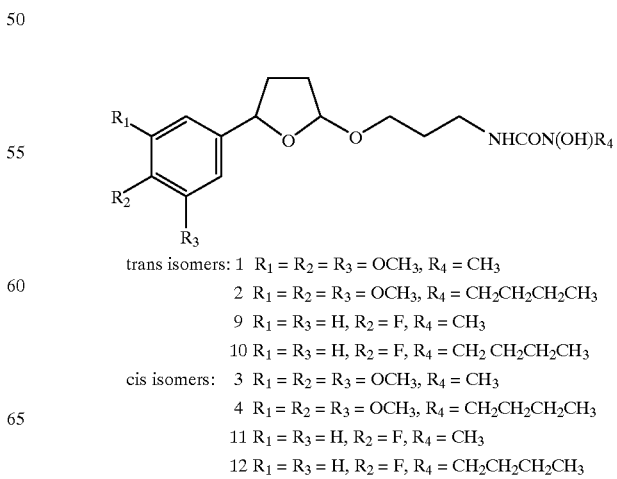

trans isomers: 1 R₁ = R₂ = R₃ = OCH₃, R₄ = CH₃
2 R₁ = R₂ = R₃ = OCH₃, R₄ = CH₂CH₂CH₂CH₃
9 R₁ = R₃ = H, R₂ = F, R₄ = CH₃
10 R₁ = R₃ = H, R₂ = F, R₄ = CH₂CH₂CH₂CH₃
cis isomers: 3 R₁ = R₂ = R₃ = OCH₃, R₄ = CH₃
4 R₁ = R₂ = R₃ = OCH₃, R₄ = CH₂CH₂CH₂CH₃
11 R₁ = R₃ = H, R₂ = F, R₄ = CH₃
12 R₁ = R₃ = H, R₂ = F, R₄ = CH₂CH₂CH₂CH₃

Scheme 7 shows the synthesis of 2-(2,4,5-trimethoxyphenyl)-5-(3-hydroxyureidyl propoxy)tetrahydrofuran (13) and 2-(4-fluorophenyl)5-(3-hydroxyureidylpropoxy)tetrahydrofuran (14, 15)
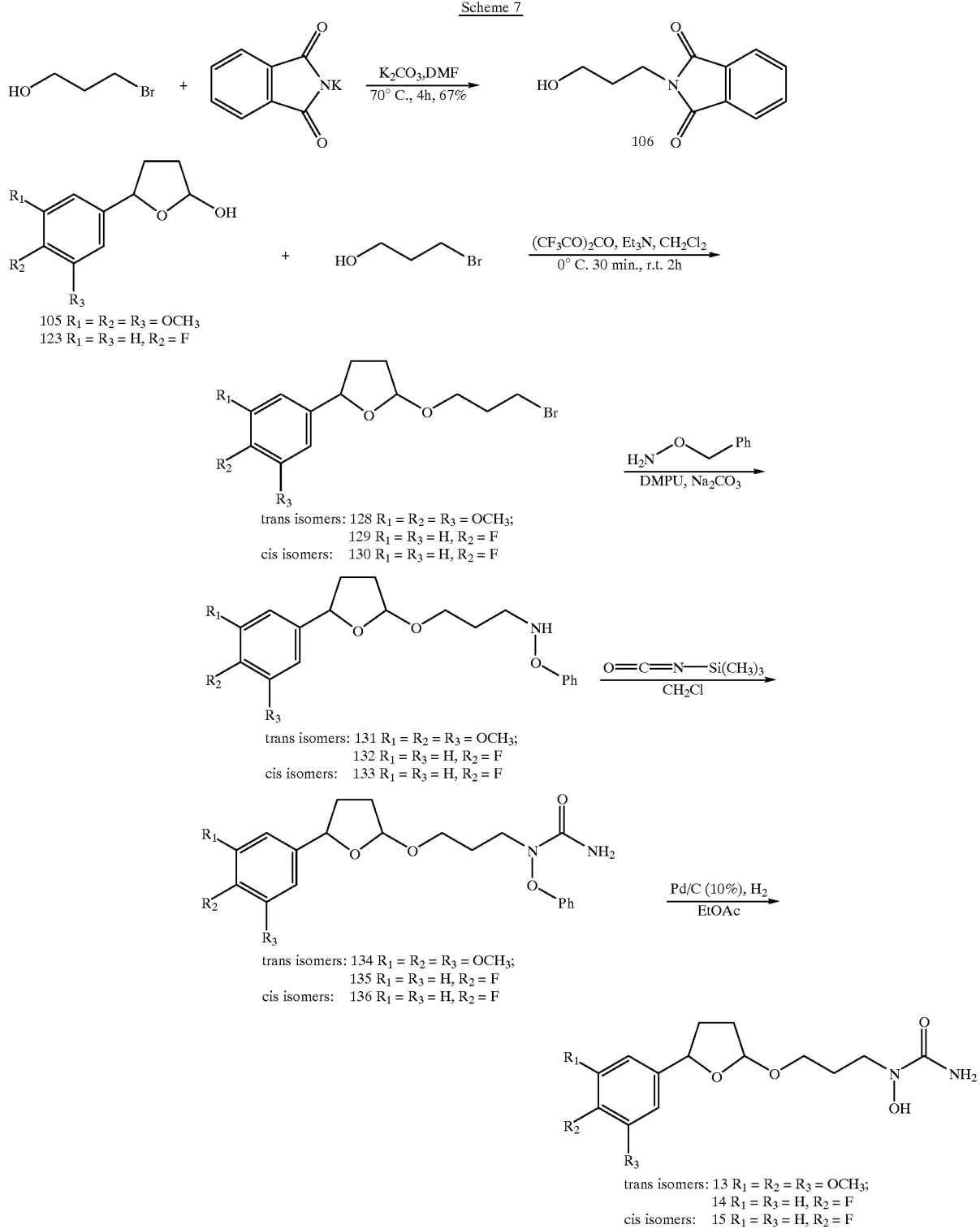

Scheme 8 shows the synthesis of 2-(3,4-dimethoxyphenyl)-5-[3-N'-substituted-N'-hydroxyureidyl propoxy]tetrahydrofuran (5–8):
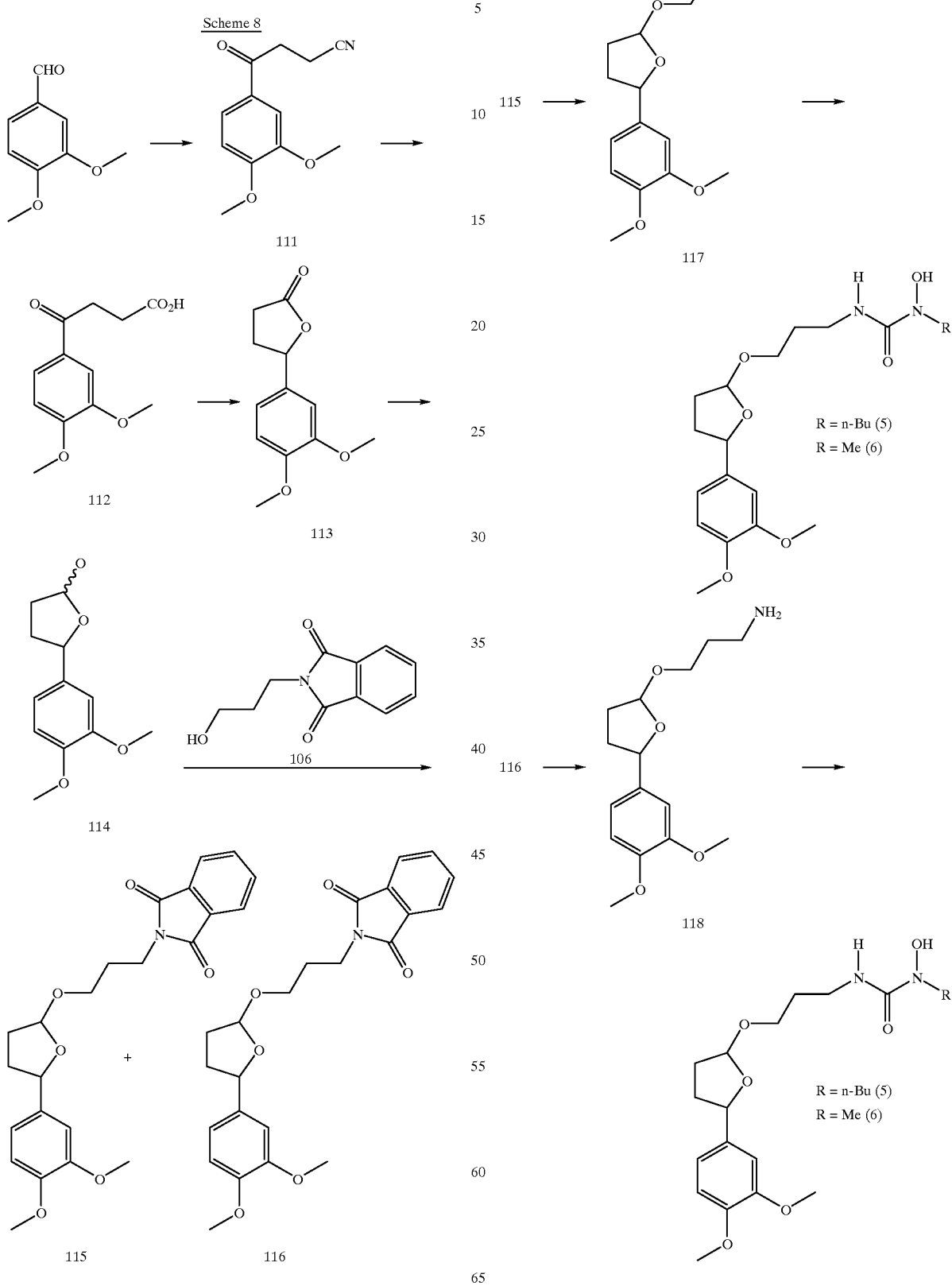

The following examples are merely illustrative, and not intended to limit the scope of the invention.

EXAMPLE 1

Preparation of 2-(3,4,5-trinethoxyphenyl)-5-[3-(N'-substituted-N'-bydroxyureidyl)propoxy] tetrabydrofuran (1-4) and 2-(4-fluorophenyl)-5-[3-(N'-substituted-N'-hydroxyureidyl) propoxy] tetrabydrofuran (9–12)

(a) Preparation of 4-(3,4,5-tri ethoxyphenyl)-4-ketone-butyric acid t-butyl enter (compound 101)

3,4,5-Trimethoxybenzaldehyde (8.0 g, 40.77 mmol), tert-butyl acrylate (5.29 g, 41.29 mmol) and the catalyst 3-ethyl-5-(2-hydroxyethyl)-4-methylthiazolium bromide (3.52 g, 13.95 mmol) were dissolved in 50 mL dimethyl formamide (DMF). To this Id solution was added 5.86 mL triethylamine. The reaction mixture was stirred at 60*C for 16 hours, cooled to room temperature and quenched by adding 10% HCl (PH 1–2), and extracted with dichloromethane. The organic layer was washed with water and saturated NaCl solution, dried over MgSO4, filtered and evaporated in vacuo to an oil. The product was purified by column chromatography (silica, 3:1 hexane/ethyl acetate) (4.5 g, 34%). $^1$H NMR (CDCl$_3$): 1.46(2,9H); 2.70(t,2H); 3.24(t, 2H); 3.92(s,9H); 7.25(s,2H).

(b) Preparation of 4-(4-fluorophenyl)-4-ketone-butyric acid t-butyl ester (compound 119)

This compound was prepared using a process similar to that set forth in Example 1(a), replacing the 3,4,5-trimethoxybenzaldehyde with 4-fluorobenzaldehyde. $^1$H NMR (CDCl$_3$): 1.45(s,9H); 2.70(t,2H); 3.23(t,2H); 7.12(m, 2H); 8.02(m,2H)

(c) Preparation of 4-(3,4,5-trimethoxyphenyl)-4-hydroxy-butyric acid t-butyl ester (compound 102)

The ketone ester 101 (1.09 g, 3.36 mmol) was added to 10 ML THF and 20 mL methanol. An aqueous solution of NaBH$_4$ (127.3 mg, 3.36 amol in 5 mL water) was added to this mixture in a dropwise manner at 0° C. The reaction mixture was stirred at room temperature for 4 hours, quenched with water and extracted with ethyl acetate. The organic layer was washed with water, saturated NaCl solution, dried over MgSO$_4$, filtered and evaporated in vacuo to provide the product (1.13 g, 103%). $^1$H NMR (CDCl$_3$): 1.46(s,9H); 2.02(m,2H); 2.37(t,2H); 3.84(s,3H); 3.88(s,6H); 4.70(m,1H); 6.58(s,2H).

(d) Preparation of 4-(4-fluorophenyl)-4-hydroxy-butyric acid t-butyl ester (compound 120)

This compound was prepared from 119 using a procedure similar to that set forth in Example l(c), replacing compound 101 with compound 119. $^1$H NMR (CDCl$_3$): 1.44(s,9H); 2.00(m,2H); 2.32(m,2H); 4.72(m,1H); 7.01(m,2H); 7.30(m, 2H).

(e) Preparation of 4-(3,4,5-trinethoxyphenyl)-δ-lactone (compound 104)

The hydroxy ester 102 (1.13 g, 3.47 mmol) was added to 4 mL methanol, 1.5 mL water and 5M aqueous sodium hydroxide solution (4.5 mL). The reaction mixture was stirred at room temperature for 30 minutes and then 12 mL of saturated aqueous NaHCO$_3$ solution was added. The aqueous phase was washed with ether, acidified to pH 1–2 by adding conc. HCl, and extracted with benzene (2×30 mL). The benzene layer was checked by TLC which showed that some of the lactone has been formed. PPTS (10 mg) was added to the benzene extract and the mixture was refluxed for 1 hour to remove water. The reaction mixture was washed with saturated NaHCO$_3$ solution and evaporated in vacuo to provide the desired lactone as a solid (700 mg, 80%). IH NMR (CDC1$_3$): 2.20(m,$_1$1H); 2.68(m,3H); 3.85(s, 3H); 3.88(s,GH); 5.46(m,1H); 6.55(s,2H).

(f) Preparation of 4-(4-fluorophenyl)-δ-lactone (compound 122)

This compound was prepared from 120 using a procedure similar to that set forth in Example 1(e), replacing compound 102 with compound 120. $^1$H NMR (CDCl$_3$): 2.20(m, 1H); 2.68(m,3H); 5.50(m,1H); 7.10(t,2H); 7.32(m,2H).

(g) Preparation of 2-(3,4,5-trimethoxyphenyl)-5-hydroxy-tetrabydrofuran (105)

Lactone 104 (6.86 g, 27.22 mmol) was dissolved in dry toluene (100 mL) and the solution was cooled to –70° C. A 1.5 M toluene solution of DIBALH (28 mL) was added to the solution in a dropwise manner. The reaction mixture was stirred at –70° C. for 1 hour. The reaction was quenched through the addition of methanol (11 mL) while maintaining a temperature of <–60° C. The mixture was warmed to –20° C. followed by the addition of saturated aqueous potassium sodium tartrate solution (96 mL) while the reaction temperature was maintained between –10 and 0° C. The reaction mixture was stirred at 0° C. for 3 hours and then the two phases were separated. The aqueous layer was extracted with ethyl acetate. The combined organic layers were washed with water, saturated NaCl solution, and then concentrated in vacuo to afford the product (6.51 g, 94%). $^1$H NMR (CDCl$_3$): 1.82–2.48(m,4H); 3.84(s,3H); 3.88(s,6H); 4.97, 5.20(m,1H); 5.65, 5.79(m,1H); 6.56, 6.70(s,2H).

(h) Preparation of 2-(4-fluorophenyl)-5-hydroxy-tetrahydrofuran (123)

This compound was prepared from 122 using a procedure similar to that set forth in Example 1(g), replacing compound 104 with compound 122. $^1$H NMR (CDCl$_3$): 1.79(m, 1H); 1.95–2.10(m,1H); 2.20–2.32(m,1H); 2.48(m,1H); 5.00 & 5.22(m,1H); 5.63 & 5.78(m,1H); 7.04(m,2H); 7.30 & 7.41(m,2H). (i) Preparation of trans and cis 2-(3,4,5-trimethoxyphenyl)-5-(3-phthalimidyl propoxy) tetrabydro-furan (compounds 107, 108) Compound 105 (1.14 g, 4.49 mmol) was dissolved in 4 mL dichloromethane. Triethylamine (681.4 mg, 6.73 mmol) was added to this solution. The reaction mixture was cooled with an ice bath and trifluoroacetic anhydride (1.41 g, 6.73 mmol) was added in a dropwise manner. The reaction mixture was stirred at 0° C. for 30 minutes and then 3-phthalimidylpropanol (106) (2.4 g, 13.26 mmol) was added. The reaction mixture was warmed to room temperature and stirred at room temperature for 2 hours. The reaction was quenched with saturated aqueous NaHC0$_3$solution and extracted with ethyl acetate. The organic layer was washed with water and saturated NaCl solution, dried over MgSO$_4$, filtered ancl evaporated in vacuo to an oil which was purified by column chromatography (silica, 2:1 hexane/ethyl acetate) (107: 522 mg (trans); 108: 271 mg (cis); 1:1 mixture of 107 and 108: 110 mg; total yield 46%). $^1$H NMR (CDCl$_3$): 107: 1.70(m,1H); 1.82(m, 1H); 2.00(m,2H); 2.02(m,1H); 2.28(m,1H); 3.46(m,1H); 3.83(s,3H); 3.84(m,3H); 3.88(s,6H); 4.99(t,1H); 5.30(dd, lH); 6.56(s,2H); 7.72Cm,2H); 7.85(m,2H). 108: 1.95(m, 3H); 2.00(m,2H); 2.20(m,1H); 3.51(m,1H); 3.83(s,3H); 3.85 (m,2H); 3.88(s,6H); 3.92(m,1H); 4.90(m,1H); 5.16(dd,1H); 6.60(s,2H); 7.72(m,2H); 7.84(m,2H).

In order to determine the stereochemistry of this molecule, an NOE difference experiment was carried out.

Trans isomer (107): In this experiment the triplet at 4.99 L ppm was irradiated with a very low rf decoupling pulse and the data work-up was done so as to only measure the presence of an increase in signal. This would represent a positive NOE effect and would indicate the close spacial relationship of these protons. In this experiment an NOE was found for the multiplet at 2.25–2.36 ppm which is a furan ring proton. Another NOE was also seen for the aromatic protons, indicating that this triplet represents the benzylic proton. There was not an NOE observed for the double doublet at 5.30 ppm indicating this was the trans isomer.

Cis isomer (108): In order to determine the stereochemistr]of this molecule an NOE difference experiment was carried out. In this experiment the multiplet at 4.88–4.93 ppm was irradiated with a very low rf decoupling pulse and the data work-up was done so as to only measure the presence of an increase in signal. This would represent a positive NOE effect and would indicate the close spacial relationship of these protons. In this experiment an NOE was found for the doublet at 5.16 ppm which is the other methine furan proton. Another NOE was also seen for the aromatic protons indicating this triplet represents the benzylic proton. There was also an NOE observed for the multiplet at 1.93–2.20 ppm for the other furan methylene protons.

(j) Preparation of 2-(4-Fluoropbonyl)-5-(3-phthalisidyl propozy) tetrahydrofuran (compounds 124, 125)

These compounds were prepared from 123 using a procedure similar to that set forth in Example 1(i), replacing compound 105 with compound 123. $^1$H NMR (CDCl$_3$): 124 (trans): 1.65(m,1H); 1.80(m,1H); 2.00(m,2H); 2.12(m,1H); 2.31(m,1H); 3.48(m,1H); 3.82(m,3H); 5.02(t,$_1$H); 5.28(dd, 1H); 7.00(t,2H); 7.29(m,2H); 7.71(m,2H); 7.85(m,2H). 125 (cis): 1.90(m,2H); 1.99(m,4H); L5 2.19(m,1H); 3.48(m,1H); 3.82(m,2H); 3.88(m,1H); 4.94(m,1H); 5.15(dd,1H); 7.00(t, 2H); 7.30(m,2H); 7.71(m,2H); 7.84(m,2H).

(k) Preparation of 3-phthalimidylpropanol (compound 106)

3-Bromopropanol (4.0 g, 28.78 mmol), potassium phthalimide (8.0 g, 43.17 mmol) and potassium carbonate (4.0 g, 28.78 mmol) were added to 20 mL DMF. The reaction mixture was stirred at 70° C. for 4 hours, quenched with water and extracted with ethyl acetate. The organic layer was washed with water, saturated NaCl solution and evaporated in vacuo to a solid which was crystallized in ethyl acetate (3.5 g, 67%).

(l) Preparation of trans and cis 2-(3,4,5-trimethoxyphenyl)-5-(3-aminopropoxy) totrahydrofuran (compounds 109, 110)

Compound 107 (455 mg, 1.03 mmol) and hydrazine monohydrate (165.3 mg, 5.16 mmol) were added to 2 mL ethanol. The reaction mixture was refluxed for 2 hours, quenched with water and extracted with dichloromethane. The organic layer was washed with water and saturated NaCl solution, dried over MgSO$_4$, filtered and evaporated in vacuo to provide the trans product 109 (225 mg, 70%). $^1$H NMR (CDCl$_3$): 1.75(m,2H); 1.78(m,1H); 1.96(m,1H); 2.20 (m,$_1$H); 2.40(m,1H); 2.82(t,2H); 3.55(m,1H); 3.81(m,$_1$H); 3.83(s,3H); 3.87(s,6H); 5.00(t,1H); 5.34(dd,1H); 6.56(s, 2H).

The cis isomer 110 was prepared from 108 using a procedure similar to that described for 109. $^1$H NMR (CDCl$_3$): 1.76(m,2H); 2.08(m,3H); 2.27(m,1H); 2.82(t,2H); 3.55(m,1H); 3.84(s,3H); 3.88(s,6H); 3.92(m,1H); 4.95(m, lH); 5.20(m,$_1$lH); 6.64(s,2H).

(m) Preparation of 2-(4-fluorophenyl)-5-(3-aminopropoxy) tetrahydrofuran (compounds 126, 127)

These compounds were prepared from 124 and 125 using a procedure similar to that set forth in Example 1(1), replacing compounds 107 and 108 with compounds 124 and 125. $^1$H NMR (CDCl$_3$): 124 (trans): 1.75(m,3H); 1.96(m, 1H); 2.20(m,1H); 2.40(m,1H); 2.82(t,2H); 3.54(m,1H); 3.83 (m,1H); 5.05(t,1H); 5.32(dd,1H);
7.01(t,2H); 7.30(m,2H). 125 (cis): 1.74(m,2H); 1.97(m, 1H);
2.05(m,2H); 2.25(m,1H); 2.77(t,2H).; 3.47(m,1H); 3.85 (m,1H);
4.95(m,1H); 5.15(dd,1H); 7.00(t,2H); 7.34(m,2H).

(n) Preparation of trans and cis 2-(3,4,5-trimethoxyphenyl)-5-[3-(N'-nethyl-N'-bydroxyureidyl) propoxy] tatrahydrofuran (compounds 1, 3)

Compound 109 (60 mg, 0.19 mol) and triphosgene (23 mg, 0.078 imol) were dissolved in 3 mL dichloromethane. Triethylamine (29.3, 0.29 ]mol) was added to this solution. The reaction mixture was refluxed for 2 hours and then cooled with ice bath. Triethylamine (34.0 mg, 0.34 mol) and methylhydroxyamine hydrochloride (32.2 mg, 0.39 mmol) were added to the cold solution. The reaction was stirred at room temperature for 16 hours, quenched with water and extracted with dichloromethane. The organic layer was washed with saturated NaCl solution and evaporated in vacuo to an oil which was purified by preparative TLC (silica, ethyl acetate) to provide the trans product 1 (51 mg, 69%). $^1$H NMR (CDCl$_3$): 1.82(m,3H); 1.95(m,1H); 2.22(m, 1H); 2.40(m,1H); 3.15(s,3H); 3.40(m,2H); 3.58(m,1H); 3.84 (s,3H); 3.85(m,1H); 3.88(s,6H); 5.00(t,1H); 5.33(m,1H); 6.32(m,1H); 6.56(s,2H); 7.37(s,1H).

The cis isomer 3 was prepared from 110 using a procedure similar to that described for 1. $^1$H NMR (CDC13): 1.83(m, 2H); 2.07(m,3H); 2.28(m,1H); 3.13(s,3H); 3.35(m,2H); 3.55 (m,1H); 3.84(s,3H); 3.87(s,6H); 3.88(m,1H); 4.97(m,1H); 5.20(m,1H); 6.22(m,1H); 6.63(s,2H); 7.37(s,lH).

(o) Preparation of 2-(4-fluorophenyl)-5-[3-(N'-methyl-N'-hydroxyureidyl)propozy ] tetrahydrofuran (compounds 9, 11)

These compounds were prepared from 126 and 127 using a procedure similar to that set forth in Example 1(n) replacing compounds 109 and 110 with compounds 126 and 127. $^1$H NMR (CDCl$_3$): 9 (trans): 1.70(m,$_1$H); 1.78(m,2H); 1.96 (m,1H); 2.19(m,1H); 2.40(m,1H); 3.10(s,3H); 3.31(m,2H); 3.51(m,1H); 3.83(m,1H); 5.05(t,1H); 5.30(dd,1H); 6.38(t, 1H); 7.01(t,2H); 7.28(m,2H). 11 (cis): 1.80(m,2H); 2.05(m, 3H); 2.24(m,1H); 3.06(s,3H); 3.30(m,2H); 3.48(m,1H); 3.86 (m,1H); 4.98(m,1H); 5.16(dd,1H); 6.30(t,1H); 7.02(t,2H); 7.31(m,2H); 8.08(bs,1H)

(p) Preparation of trans and cis 2-(3,4,5-trimethoxyphenyl)-5[3-(N'-n-butyl-N'-hydroxyureidyl) propoxy] tetrahydrofuran (compounds 2,4)

Compound 109 (60 mg, 0.19 mmol) and triphosgene (23 mg, 0.078 mmol) were dissolved in 3 mL dichloromethane. Triethylamine (29.3, 0.29 mmol) was added to this solution. The reaction mixture was refluxed for 2 hours and then cooled with ice bath. Butylhydroxyamine (51.4 mg, 0.29 mmol) was added to the cold solution. The reaction mixture was stirred at room temperature for 16 hours, quenched with water and extracted with dichloromethane. The organic layer was washed with saturated NaCl solution and evaporated in vacuo to an oil. The trans product 2 was separated by preparative TLC (silica, ethyl acetate) (46.9 mg, 579%). $^1$H NMR (CDCl$_3$): 0.93(t,3H); 1.35(m,2H); 1.58(m,2H); 1.81 (m,3H); 1.96(m,1H); 2.21(m,1H); 2.40(m,1H); 3.38(m,2H); 3.50(m,2H); 3.57(m,1H); 3.83(s,3H); 3.85(m,1H); 3.88(s, 6H); 5.00(t,1H); 5.32(m,$_1$H); 6.32(m,1H); 6.56(s,2H).

The cis isomer 4 was prepared from 110 using a procedure similar to that described for 2. $^1$H NMR (CDCl$_3$): 0.92(t, 3H); 1.32(m,2H); 1.58(m,2H); 1.81(m,2H); 2.08(m,3H); 2.28(m,1H); 3.35(m,2H); 3.47(m,2H); 3.54(m,1H); 3.84(s, 3H); 3.87(s,6H); 3.88(M,1H); 4.97(m,1H); 5.20(m,1H); 6.22(m,1H); 6.63(s,2H).

(q) Preparation of 2-(4-fluorophenyl)-5[3-(N'-n-butyl-N'-hydroxynreidyl)propoxy] tetrabydrofuran (compounds 10,12)

These compounds were prepared from 126 and 127 using a procedure similar to that set forth in Example 1(p) replacing compounds 109 and 110 with compounds 126 and 127. $^1$H NMR (CDCl$_3$): 10 (trans): 0.90(t,3H); 1.30(m,2H); 1.55 (m,2H); 1.70(m,1H); 1.78(m,2H); 1.96(m,1H); 2.19(m,1H); 2.40(m,1H); 3.31(m,2H); 3.44(m,2H); 3.52(m,1H); 3.82(m, 1H); 5.05(t,$_1$H); 5.30(dd,1H); 6.32(t,1H); 7.00(t,2H); 7.28 (m,2H); 7.55(bs,$_1$H). 12 (cis): 0.90(t,3H); 1.30(m,2H); 1.52 (m,2H); 1.80(m,2H); 2.04(m,3H); 2.24(m,1H); 3.30(m,2H); 3.40(m,2H); 3.48(m,$_1$1H); 3.85(m,1H); 4.98(t,1H); 5.16(dd, 1H); 6.27(t,1H); 7.03(t,2H); 7.32(m,2H); 7.53(bs,1H).

EXAMPLE 2

Preparation of 2-(3,4-Diaethoxyphenyl)-5-[3-N'-substituted-N'-hydroxyureidyl propoxy]tetrahydrofuran (5–8)

(a) Preparation of 4-(3',4'-dimethoxyphenyl)-4-oxobutyronitrile (111).

A single portion of neat acrylonitrile (3.2 ml, 0.048 mol) and triethylamine (5 ml, 0.11 mol) was added to a stirred mixture of 3,4-dimethoxybenzaldehyde (7.8 g, 0.047 mol) and 3-benzyl-5-(2-hydroxyethyl)-4-methylthiazolium chloride (5.3 g, 0.02 mol) in dry dimethylformamide (25 ml) under argon. The mixture was left overnight at room temperature. The reaction was diluted with water and extracted with ethyl acetate (3×100 ml). The organic extract was washed with water (3×100 ml), brine (3×100 ml) and the solvent was removed under reduced pressure to give an amber oil. Analysis by TLC (silica gel; ethyl acetate:hexanes, 1:1) revealed a mixture of three spots at Rf 0.80 (starting aldehyde), 0.50 (Compound 1) and 0.30 (unknown by-product). The sample was purified by column (flash) chromatography on silica gel 60 (230–400 mesh) and eluted with ethyl acetate:hexanes (1:1) to give the desired compound (2.26 g, 22%) as a yellow solid. $^1$H NMR (CDCl$_3$) 2.78 (t, 2H, J=8 Hz), 3.33 (t, 2H, J=8 Hz), 3.96 (s, 3H), 3.98 (s, 3H), 6.90(d, 1H, J=8.5 Hz), 7.52 (d, J=2 Hz, 2H), 7.58 (dd, J=2 and 8 Hz, 2H).

(b) Preparation of 4-(3',4'-dinethoxyphenyl)-4-oxobutyric acid (112).

A stirred solution of 4-(3',4'-dimethoxyphenyl)-4-oxobutyronitrile (111) (2.26 g, 0.01 mol) in acetic acid (15 ml) and hydrochloric acid (12 N, 40 ml) was heated at reflux for 1.5 hours and cooled to room temperature. The solvent was removed under reduced pressure to give a brown solid. Recrystallization from water gave 112 as light tan crystals (1.57 g, 66%). 1H NMR (CDCl$_3$) 2.80 (t, J=7.5 Hz, 2H), 3.30 (t, J=7.5 Hz, 2H), 3.94 (E, 3H), 3.96 (s, 3H), 6.89 (d, 1H, J=9 Hz), 7.55 (d, 1H, J=1 Hz) and 7.64 (dd, IH, 1 and 9 Hz). (c) Preparation of 4-(3',4'-dinethoxyphenyl) butyrolactone (113).

A solution of sodium borohydride (0.89 g, 0.023 mol) in water (4 ml) was added dropwise (ca. 5 min) to a stirred solution of 112 (2.8 g, 0.012 mol) in dry, freshly distilled tetrahydrofuran (40 ml) and methanol (20 ml) under argon. The reaction was left overnight at room temperature. Analysis by TLC (silica gel; ethyl acetate:methanol:acetic acid, 9.5:0.5:few drops) indicated the presence of starting material. An additional charge of sodium borohydride (0.5 g, 0.013 mol) in I<water (2 ml) was added dropwise and the reaction left at room temperature for three hours. Analysis by TLC (same system as above) indicated the absence of starting material. The reaction was quenched with hydrochloric acid (6 N, 25 ml) and left at room temperature for 15 minutes. The mixture was extracted with ethyl acetate (3×75 ml). The organic extract was washed with water (3×75 ml), brine (3×75 ml) and the solvent removed under reduced pressure to give a tan solid (2.0 g, 75%). $^1$H NMR (CDCl$_3$) 2.18–2.25 (m, 1H), 2.59–2.70 (m, 3H), 3.89 (s, 3H), 3.90 (s, 3H), 5.44–5.49 (m, 1H) and 6.82–6.87 (m, 3H).

(d) Preparation of 4-(31,41-Cilethoxyphenyl)butyrolactol (114).

A solution of diisobutylaluminum hydride (1.5 M, 9 ml, 13.5 mmol) was added in a dropwise manner (ca. 30 min.) to 113 (2.0 g, 9 mmol) in dry toluene (40 ml) under argon which was cooled by a dry ice-acetone bath. The reaction was stirred at −78° C. for one hour. Analysis by TLC (silica gel; ethyl acetate:hexanes, 1:1) revealed the absence of starting material and the presence of a new spot at Rf 0.38. The reaction was quenched with methanol (20 ml) and slowly warmed to 0° C. A saturated solution of sodium potassium tartrate (50 ml) was added and stirred at 0° C. for 45 minutes., The mixture was extracted with ethyl acetate (3×100 ml) and the organic extract washed with water (3×75 ml) and brine (3×75 ml). Removal of the solvent under reduced pressure gave a dark abber oil (1.7 g, 84%). IH NMR (CDCl$_3$) (mixture of cis and trans isomers) 1.71–2.49 (m, 8H), 2.91 (br s, 1H), 3.09 (br s, 1H), 3.89 (s, 6H), 3.90(s, 6H), 4.97 (m, 1H), 5.19 (t, J=7Hz, 1H), 5.62 (m, 1H), 5.77 (m, 1H) and 6.82–7.28 (m, 6H).

(e) Preparation of N-(3-hydroxypropyl)phthalimide (106).

A mixture of 3-bromopropanol (4 g, 0.029 mol), potassium ma phthalate (8 g, 0.043 mol) and potassium carbonate (4 g, 0.029 mol) in dry DMF (50 ml) was stirred and heated at 70° C. for four hours. The mixture was diluted with water (100 ml) and extracted with ethyl acetate (3×75 ml). The organic extract was washed with water (3×100 ml) and dried (Na$_2$SO$_4$). Removal of the solvent under reduced pressure left a white solid which was extracted with benzene. The benzene extract was evaporated to a white solid and recrystallized from ethyl acetate-hexanes to give white crystals (1.27 g, 24%).

(f) Preparation of trans and cis 2-(3',4'-dimethoxyphenyl)-5-[3-(N-phthaloyl)]propoxytetrahydrofuran (115 and 116).

Triflic anhydride (0.68 ml, 4.8 mmol) was added in a single portion to a stirred solution of 114 (0.72 g, 3.2 mmol) in dry dichloromethane (20 ml) and triethylamine (0.68 ml, 4.9 mmol) under argon which was cooled using an ice bath. The reaction was stirred at 0° C. for 30 minutes. N-(3-hydroxypropyl)phthalimide (106) (1.27 g, 7 imol) was added to the reaction mixture and the solution was allowed to warm to room temperature and left at this temperature for two hours. The solution was quenched with aqueous sodium bicarbonate solution (saturated, 25 ml) and extracted with ethyl acetate (3×50 ml), brine (3×50 ml) and dried (sodium sulfate). Removal of the solvent under reduced pressure left an amber oil (2.02 g). Analysis of the oil by TLC (silica gel; ethyl acetate:hexanes, 1:1) revealed the presence of four spots at Rf 0.80, 0.60, 0.50 and 0.35. The spots at Rf 0.60 and 0.50 were in a 2:1 ratio. The sample was purified by column chromatography (flash) on silica gel (230–400 mesh) and eluted with ethyl acetate:hexanes (3:7) to give first the substance at Rf 0.60 as a clear and colorless oil (0.40 g, 30%), identified as trans 2-(3',4'-dimethoxyphenyl)-5-(3-(N-phthaloyl)]-propoxytetrahydrofuran (115) (0.40 g, 30%). $^1$H NMR (CDCl$_3$) 1.34–1.94 (m, 2H), 1.96–2.05 (m, 2H), 2.09–2.20 (m, 1H), 2.25–2.36 (m, 1H), 3.46–3.53 (m, 1H), 3.84 (t, 9Hz, 2H), there is also a hidden 1 proton multiplet here, 3.88 (s, 3H), 3.91 (s, 3H), 5.01 (t, 7.3 Hz, 1H), 5.30 (dd, J=2 and 5 Hz, 1 Hz), 6.82–6.90 (m, 3 H), 7.71–7.74 (m, 2H) and 7.84–7.88 (m, 2H).

In order to determine the stereochemistry of this molecule and NOE difference experiment was carried out. In this experiment the triplet at 5.01 ppm was irradiated with a very low rf decoupling pulse and the data work-up was done so as to only measure the presence of an increase in signal. This would represent a positive NOE effect and would indicate the close spatial relationship of these protons. In this experiment an NOE was found for the multiplet at 2.25–2.36 ppm which is a furan ring proton. Another NOE was also seen for the aromatic protons Warm indicating this triplet presents the benzylic proton. There was not an NOE observed for the double doublet at 5.30 ppm indicating this was the trans isomer.

Continued elution with the same solvent system gave the spot at Rf 0.50 as a colorless oil (0.21 g, 15%), identified as cis 2-(3',4,-dimethoxyphenyl)-5-[3-(N-phthaloyl)]propoxytetrahydrofuran (116). $^1$H NMR (CDCl$_3$) 1.92–2.12 (m, 6H), 3.44–3.52 (m, 1H), 3.86 (s, 3H), 3.88 (s, 3H), 3.76–3.93 (m, 3H), 4.89–4.94 (a, 1H), 5.35 (d, J=4 Hz), 6.89 (d, J=8 Hz), 6.87 (dd, J=2 and 8 Hz), 6.92 (d, J=2 Hz), 7.69–7.72 (m, 2H) and 7.82–7.85 (m, 2H).

In order to determine the stereochemistry of this molecule an NOE difference experiment was carried out. In this experiment the multiplet at 4.89–4.94 ppm was irradiated with a very low rf decoupling pulse and the data work-up was done so as to only measure the presence of an increase in signal. This would represent a positive NOE effect and would indicate the close spatial relationship of these protons. In this experiment an NOE was found for the doublet at 5.35 ppm which is the other methine furan proton. This indicates that this molecule is the cis isomer. Another NOE was also seen for the aromatic protons indicating this triplet presents the benzylic proton. There was also an NOE present for the multiplet at 1.92–2.12 ppm which contains the other furan methylene protons.

The chromatography also yielded a mixture of 115 and 116 (0.342 g, 26%).

(g) Preparation of trans 2-(3',4'-diethoxyphenyl)-5-(3-aminopropoxy)tetrahydrofuran (117).

Neat hydrazine hydrate (150 µl, 3.2 mmol) was added to a stirred solution of 115 (253 mg, 0.62 mmol) in absolute ethanol (1.5 ml). The solution was heated at reflux for 5 minutes whereupon a white solid precipitated out of solution. The mixture was heated at reflux for two hours. Analysis by TLC (silica gel; ethyl acetate:hexanes, 1:1) revealed the absence of starting material and the presence of a spot at the origin. The reaction was quenched with water (10 ml) and extracted with dichloromethane (5×10 ml). The organic phase was washed with water (2×10 ml), brine (2×10 ml) and dried (sodium sulfate). Removal of the solvent under reduced pressure left a colorless oil (150 mg, 86%). $^1$H NMR (CDCl$_3$) 1.25 (br s, 2H), 1.68–1.78 (m, 3H), 1.81–1.98 (mn, 1H), 2.14–2.2 (m, 1H), 2.3–2.36 (m, 1H), 2.80 (t, J=6.5Hz, 2H), 3.47–3.55 (m, 1H), 3.78–3.87 (m, partially hidden, 1H), 3.86 (s, 3H), 3.88 (s, 3H), 4.99 (t, J=7 Hz, 1H), 5.31 (dd, J=2 and 6 Hz, 1H), 6.80–6.88 (m, 3H).

(h) Preparation of cis 2-(3',4'-diaethoxyphenyl)-5-(3-aminopropoxy)tetrahydrofuran (118).

Neat hydrazine hydrate (125 µl, 2.57 mmol) was added to a stirred solution of 116 (210 mg, 0.51 mmol) in absolute ethanol (3.0 ml). The solution was heated at reflux for 5 minutes whereupon a white solid precipitated out of solution. The mixture was heated at reflux for two hours. Analysis by TLC (silica gel; ethyl acetate:hexanes, 1:1) revealed the absence of starting material and the presence of a spot at the origin. The reaction was quenched with water (10 ml) and extracted with dichloromethane (5×10 ml). The organic phase was washed with water (2×10 ml), brine (1×10 ml) and dried (sodium sulfate). Removal of the solvent under reduced pressure left a stiff oil (105 mg, 73%). $^1$H NMR (CDCl$_3$) 1.45 (br s, 2H), 1.73–1.78 (m, 2H), 2.01–2.12 (m, 3H), 2.19–2.29 (m, 1H), 2.81 (t, J=7 Hz, 2H), 3.48–3.53 (a, 1H), 3.85–3.93 (m, partially hidden, 1H), 3.88 (s, 3H), 3.90 (s, 3H), 4.96–5.01 (m, 1H), 5.17 (dd, J=3 and 6 Hz, 1H), 6.83 (d, J=8 Hz, 1H), 6.89 (dd, J=2 and 8 Hz, 1H) and 6.96 (d, J=2 Hz, 1H).

(i) Preparation of trans 2-(3',4'-dimethoxyphenyl)-5-[3-(M-butyl-N-hydroxyureidyl)propoxy]tetrahydrofuran (S).

Triethylamine (32 µl, 0.22 mmol) and then triphosgene (19 mg, 0.06 mmol) were added to a stirred solution of 117 (53 mg, 0.19 mmol) in dry dichloromethane (3 ml) under argon. The solution was heated at reflux for 30 minutes and cooled to room temperature. Solid n-butylhydroxylamine (34 mg, 0.38 mmol) was added in one portion to the solution which was left overnight at room temperature. The reaction was quenched with water (10 ml) and extracted with dichloromethane (3×10 ml). The combined organic phase was washed with aqueous sodium bicarbonate solution (saturated, 3×10 ml) and dried (sodium sulfate). Analysis by TLC (silica gel, ethyl acetate) revealed a complex mixture Rf 0.90, 0.50, 0.25 and 0.00. The sample was purified by column (flash) chromatography on silica gel 60 (230–400 mesh) and eluted with ethyl acetate to give the spot at Rf 0.50 as an opaque oil (8 mg, 11%). $^1$H NMR (CDCl$_3$) 0.92 (t, J=7 Hz, 3H), 1.27–1.39 (m, 2H), 1.51–1.61 (m, 2H), 1.71–1.86 (m, 3H), 1.88–2.15 (m, 1H), 2.17–2.29 (m, 1H), 2.32–2.42 (m, 1H), 3.28–3.58 (m, 4H), 3.81–3.94 (m, partially hidden, 2H), 3.87 (s, 3H), 3.90 (s, 3H), 5.49–5.05 (m, 1H), 5.31–5.38 (m, 1H), 6.28–6.34 (m, 1H) and 6.81–6.86 (m, 3H). IR (film) 3407, 3193, 2933, 1640, 1516, 1263, 1029 cm$^1$ (j) Preparation of trans 2-(3',4'-diethoxyphenyl)-5-[3-(N-methyl-N-hydroxyureidyl)propoxy]tetrahydrofuran (C).

Triphosgene (12 mg, 0.04 mmol), followed immediately by triethylamine (17 µl, 0.12 mmol) was added to a stirred solution of 117 (32 mg, 0.011 mmol) in dry dichloromethane (3 ml) under argon. The solution was heated at reflux for 2 hours, cooled to room temperature and placed in an ice bath. Neat triethylamine (32 µl, 0.23 mmol) followed by methylhydroxylamine hydrochloride salt (19 mg, 0.23 mmol) was added to the reaction mixture. The reaction was left overnight at room temperature. It was then quenched with water (10 ml) and extracted with dichloromethane (3×10 ml). The organic extract was washed with water (3×10 ml), brine (3×10 ml) and the solvent was removed under reduced pressure to give an amber oil. Analysis by TLC (silica gel, ethyl acetate) revealed only one new spot at Rf 0.30. The sample. was purified by column (flash) chromatography on silica gel 60 (230–400 mesh) and eluted with ethyl acetate to give the desired compound as an amber oil (12 mg, 30%). $^1$H NMR (CDCl$_3$) 1.73–1.84 (m, 2H), 1.90–2.01 (m, 1H), 2.03–2.13 (m, 1H), 2.18–2.29 (m, 1H), 2.32–2.43 (m, 1H), 3.13 (s, 3H), 3.30–3.44 (m, 2H), 3.49–3.59 (m, 1H), 3.82–3.92 (m, partially hidden, 3H), 3.88 (s, 3H), 3.91 (m, 3H), 4.96–5.04 (m, 1H), 5.34 (dd, J=2 and 5 Hz, 1H), 6.34 (br t, 5Hz, 1H) and 6.82–6.68 (m, 3H). IR (film) 3407, 3229, 2935, 1636, 1516, 1263 and 1029 cm$^{-1}$.

(k) Preparation of cis 2-(3',4'-diaethoxyphenyl)-5-[3-(N-butyl-N-hydroxyureidyl)propoxy]tetrahydrofuran (7).

Triphosgene (18 mg, 0.06 mmol), followed immediately by triethylamine (80 µl, 0.57 mmol) were added to a stirred solution of 118 (50 mg, 0.18 mmol) in dry dichloromethane (3 ml) under argon. The solution was heated at reflux for 2 hours, cooled to room temperature and placed in an ice bath. Neat triethylamine (50 µl, 0.35 mmol) was added, followed by solid n-butylhydroxylamine (32 mg, 0.36 mmol). The reaction was left overnight at room temperature. It was then quenched with water (10 ml) and extracted with dichloromethane (3×10 ml). The organic extract was washed with water (3×10 ml), brine (3×10 ml), and the solvent was removed under reduced pressure to give an amber oil. Analysis by TLC (silica gel, ethyl acetate) revealed two new spots in approximately equal amounts at Rf 0.85 and 0.45. The sample was purified by column (flash) chromatography on silica gel 60 (230–400 mesh) and eluted with ethyl acetate to give first the spot at Rf 0.85 as an amber oil (26 mg). Continued elution with the same solvent system then gave the title compound as an amber oil (25 mg, 35%). $^1$H NMR (CDCl$_3$) 1.1 (t, J=7 Hz, 3H), 1.25–1.37 (m, 2H), 1.49–1.59 (m, 2H), 1.76–1.84 (m, 2H), 1.99–2.1 (m, 3H), 2.19–2.26 (m, 1H), 3.26–3.54 (m, 5H), 3.84–3.92 (m, partially hidden, 1H), 3.87 (s, 3H), 3.88 (s, 3H), 4.94–5.02 (m, 1H), 5.17 (d, J=4 Hz, 1H), 6.24 (t, J=4 Hz, 1H), 6.52 (br s, 1H), 6.83 (d, J=8 Hz, 1H) and 6.89–95 (m, 2H). IR (film) 2913, 1640, 1570, 1463, 1262, 1139 and 1031 cm$^{-1}$.

(l) Preparation of cis 2-(3',4'-4oethoxyphenyl)-5-[3-(N-methyl-N-hydroxyureidyl)propoxy]tetrahydrofuran (8).

Triphosgene (20 mg, 0.07 mmol), followed immediately by triethylamine (80 μl, 0.57 mmol)were added to a stirred solution of 118 (56 mg, 0.2 mmol) in dry dichloromethane (3 ml) under argon. The solution was heated at reflux for 2 hours, cooled to room temperature and placed in an ice bath. Neat triethylamine (80 μl, 0.57 mmol) was added followed by solid methyl hydroxylamine hydrochloride salt (32 mg, 0.39 mmol). The reaction was left overnight at room temperature. It was then quenched with water (10 ml) and extracted with dichloromethane (3×10 ml). The organic extract was washed with water (3×10 ml), brine (3×10 ml), and the solvent was removed under reduced pressure to give an amber oil. Analysis by TLC (silica gel, ethyl acetate) revealed one spot at rf 0.30 and some material at the origin. The sample was purified by column (flash) chromatography on silica gel 60 (230–400 mesh) and eluted with ethyl acetate to give the title compound as an amber oil (30 mg, 42%). $^1$H NMR (CDCl$_3$) 1.76 (m, 2H), 1.98–2.10 (m, 3H), 2.18–2.26 (m, 1H), 3.07 (s, 3H), 3.25–3.37 (m, 2H), 3.46–3.54 (m, 1H), 3.85–3.90 (m, partially hidden, 1H), 3.87 (s, 3H), 3.88 (s, 3H), 4.93–5.00 (m, 1H), 5.16 (d, J=4 Hz, 1H), 6.27 (t, J=5 Hz, 1H), 6.83 (d, J=8 Hz, 1H) and 6.88–6.93 (m, 2H). IR (neat) 2933, 1643, 1518, 1261 and 1029 cm$^{-1}$.

EXAMPLE 3

Preparation of 2-(2,4,5-trimethoxyphenyl)-5-(3-hydroxyureidyl propoxy)tetrahydrofuran (13) and 2-(4-fluorophenyl)S-(3-hydroxyureidylpropoxy)tetrahydrofuran 599 (14, 15)

(a) Preparation of 2-(3,4,5-trimethoxyphenyl)-5-(3-bromopropoxy) tetrahydrofuran (compound 128)

Compound 105 (1.0 g, 3.94 mmol) was dissolved in 4 mL dichloromethane. Triethylamine (597 mg, 5.90 mmol) was added tc this solution. The reaction mixture was cooled with an ice bath, and trifluoroacetic anhydride (1.24 g, 5.90 mmol) was added dropwise. The reaction mixture was stirred at 0° C. for 30 minutes and then 3-bromopropanol (1.84 g, 13.27 mmol) was added. The reaction mixture was warmed to room temperature and stirred at room temperature for 2 hours. The reaction was quenched with saturated aqueous NaHCO$_3$solution and extracted with ethyl acetate. The organic layer was washed with water and saturated NaCl solution, dried over MgSO$_4$, filtered and evaporated in vacuo to an oil which was purified by column chromatography (silica, 4:1 hexane/ethyl acetate) (128: 430 mg and its cis isomer 250 mg; total yield 46%). $^1$H NMR (CDCl$_3$): 128 (trans): 1.77(m,1H); 1.98(m,1H); 2.15(m,2H); 2.20(m,1H); 2.40(m,1H); 3.53(t,2H); 3.60(m,1H); 3.83(s,3H); 3.87(m,1H); 3.89(s,6H); 5.01(t,1H); 5.35(dd,1H); 6.57(s,2H).

(b) Preparation of 2-(4-fluorophenyl)-5-(3-bromopropoxy) tetrahydrofuran (compounds 129, 130)

These compounds were prepared from 123 using a procedure similar to that set forth in Example 3(a), replacing compound 105 ;L with compound 123. $^1$H NMR (CDCl$_3$): 129 (trans): 1.72(m,1H); 1.98(m,1H); 2.14(m,2H); 2.20(m, 1H); 2.40(m,1H); 3.53(t,2H); 3.60(m,1H); 3.89(m,1H); 5.06 (t,1H); 5.34(m,1H); 7.02(t,2H); 7.30(m,2H). 130 (cis): 1.98 (m,1H); 2.07(m,2H); 2.14(m,2H); 2.26(m,1H); 3.52(t,2H); 3.58(m,1H); 3.93(m,1H); 5.00(m,1H); 5.20(dd,1H); 7.03(t, 2H); 7.35(m,2H).

(c) Preparation of 2-(3,4,,5-trimethoxyphenyl) -5(3-O-benzylhydroxylaminopropoxy) tetrahydrofuran (compounds 131)

Compound 128 (260 mg, 0.69 mmol) was dissolved in 2 mL 1,3-dimethyl-3,4,5,6-tetrahydro-2-(1H)-pyrimidinone (DMPU). Sodium carbonate (220.4 mg, 2.08 mmol) and benzylhydroxylamine hydrochloride (166 mg, 1.04 mmol) were added to this solution.

The reaction was stirred at 80*C for 16 hours, quenched with water and extracted with ethyl acetate. The organic layer was washed with water and saturated sodium chloride solution, dried over MgSo$_4$, filtered and evaporated to an oil which was purified by column (flash) chromatography using ethyl acetate as a solvent (114 mg, 40%). $^1$H NMR (CDCl$_3$): 1.72(m,1H); 1.82(m,2H); 1.92(m,1H); 2.18(m,1H); 2.36(m, 1H); 3.06(t,2H); 3.52(m,1H); 3.81(m,1H); 3.83(s,3H); 3.87 (s,6H); 4.71(s,2H); 4.98(t,1H); 5.30(dd,1H); 6.55(s,2H); 7.35(m,5H).

(d) Preparation of 2-(4-fluorophenyl)-5-(3-O-bensylhydroxylaninopropoxy) tetrahydrofuran (compounds 132,133)

These compounds were prepared from compounds 129 and 130 using a procedure similar to that set forth in Example 3(c), replacing compound 128 with compounds 129 and 130. $^1$H NMR (CDCl$_3$): 132 (trans): 1.70(m,1H); 1.83(m,2H); 1.94(m,1H); 2.17(m,1H); 2.38(m,1H); 3.07(t, 2H); 3.52(m,1H); 3.82(m,2H); 4.71(s,2H); 5.02(t,1H); 5.30 (ss,1H); 7.02(t,2H); 7.30(m,2H); 7.36(m,5H). 133 (cis): 1.85(m,2H); 1.96(m,1H); 2.05(m,2H); 2.26(m,1H); 3.05(t, 2H); 3.50(m,1H); 3.88(m,2H); 4.70(s,2H); 4.99(m,1H); 5.17 (dd,1H); 5.50(bs,1H); 7.00(t,2H); 7.35(m,7H)

(e) Preparation of 2-(3,4,5-triaethoxyphenyl)-5-(3-O-benuylhydrozyureidylpropoxy) tetrabydrofuran (compounds 134)

Compound 131 (114 mg, 0.27 mmol) was dissolved in 3 mL dichloromethane. Trimethylsilyl isocyanate (47.6 mg, 0.41 mmol) was added to this solution. The reaction was stirred at room temperature for 16 hours and then refluxed for 4 hours. The reaction was quenched with saturated ammonium chloride solution, extracted with ethyl acetate and evaporated to an oil. The product was isolated by preparative TLC using ethyl acetate as solvent. $^1$H NMR (CDCl$_3$): 1.72(m,1H); 1.94(m,3H); 2.16(m,1H); 2.38(m, 1H); 3.50(m,1H); 3.62(m,2H); 3.80(m,1H); 3.82(s,3H); 3.84 (s,6H); 4.81(s,2H); 4.99(t,1H); 5.30(m,3H); 6.54(s,2H); 7.37(s,5H).

(f) Preparation of 2-(4-fluorophenyl)-5-(3-O-benzylhydroxyureidylpropoxy) tetrahydrofuran (compounds 135, 136)

These compounds were prepared from 132 and 133 using a procedure similar to that set forth in Example 3(e), replacing compounds 131 with compounds 132 and 133. $^1$H NMR (CDCl$_3$): 135 (trans): 1.70(m,1H); 1.93(m,3H); 2.16 (m,1H); 2.39(m,1H); 3.50(m,1H); 3.62(m,2H); 3.80(m,1H); 4.82(s,2H); 5.04(t,1H); 5.30(dd,1H); 5.35(bs,2H); 7.00(t, 2H); 7.29(m,2H); 7.38(s,5H). 136 (cis): 1.98(m,4H); 2.08 (m,1H); 2.25(m,1H); 3.48(m,1H); 3.62(m,2H); 3.83(m,1H); 4.81(s,2H); 4.98(m,1H); 5.17(dd,1H); 5.42(bs,1H); 7.00(t, 2H); 7.33(m,2H); 7.38(s,5H).

(g) Preparation of 2-(3,4,5-trinethoxyphenyl)-5(3-hydroxyureidylpropoxy) tetrahydrofuran (compounds 13)

Compound 134 (90 mg, 0.19 mmol) was dissolved in 2 mL ethyl acetate and then Pd/C (10%) (18 mg) was added. The reaction mixture was hydrogenated at balloon pressure for 16 hours. The reaction was filtered and the filtrate was concentrated. The product was isolated by preparative TLC using ethyl acetate as solvent (68 mg). $^1$H NMR (CDCl$_3$): 1.75(m,1H); 1.91(m,2H); 1.95(m,1H); 2.20(m,$_1$H); 2.37(m, 1H); 3.58(m,1H); 3.66(m,2H); 3.81(s,3H); 3.85(m,1H); 3.87 (s,6H); 5.00(t,1H); 5.35(dd,1H); 5.41(bs,2H); 6.53(s,2H); 8.39(s,1H).

(h) Preparation of 2-(4-fluoraphenyl)-5-(3-hydrozyureidylpropoxy) tetrahydrofuran (compounds 14, 15)

Compounds 14 and 15 were prepared from 135 and 136 using a procedure similar to that set forth in Example 3(g), replacing compound 134 with compounds 135 and 136. $^1$H NMR (CDCl$_3$): 14 (trans): 1.72(m,1H); 1.93(m, 3H); 2.20 (m,1H); 2.38(m,1H); 3.58(m,1H); 3.67(m,2H); 3.85(m,1H); 5.05(t,1H); 5.33(dd,1H); 5.48(bs,2H); 7.00(t,2H); 7.28(m, 2H); 8.48(bs,1H). 15 (cis): 1.92(m,2H); 2.01(m,1H); 2.10 (m,2H); 2.26(m,1H); 3.53(m,1H); 3.64(m,2H); 3.87(m,1H); 4.98(m,1H); 5.20(dd,1H); 5.43(bs,2H); 7.01(m,2H); 7.31 (m,2H); 8.43(bs,lH).

EXAMPLE 4

Preparation of Trans-2-{3-(N-hydroxyureidyl)-but-1-ynyl}-5-(4-fluorophenyl)tetrahydrofuran (207)

A synthetic scheme for the production of compound 207 is illustrated in Scheme 9.

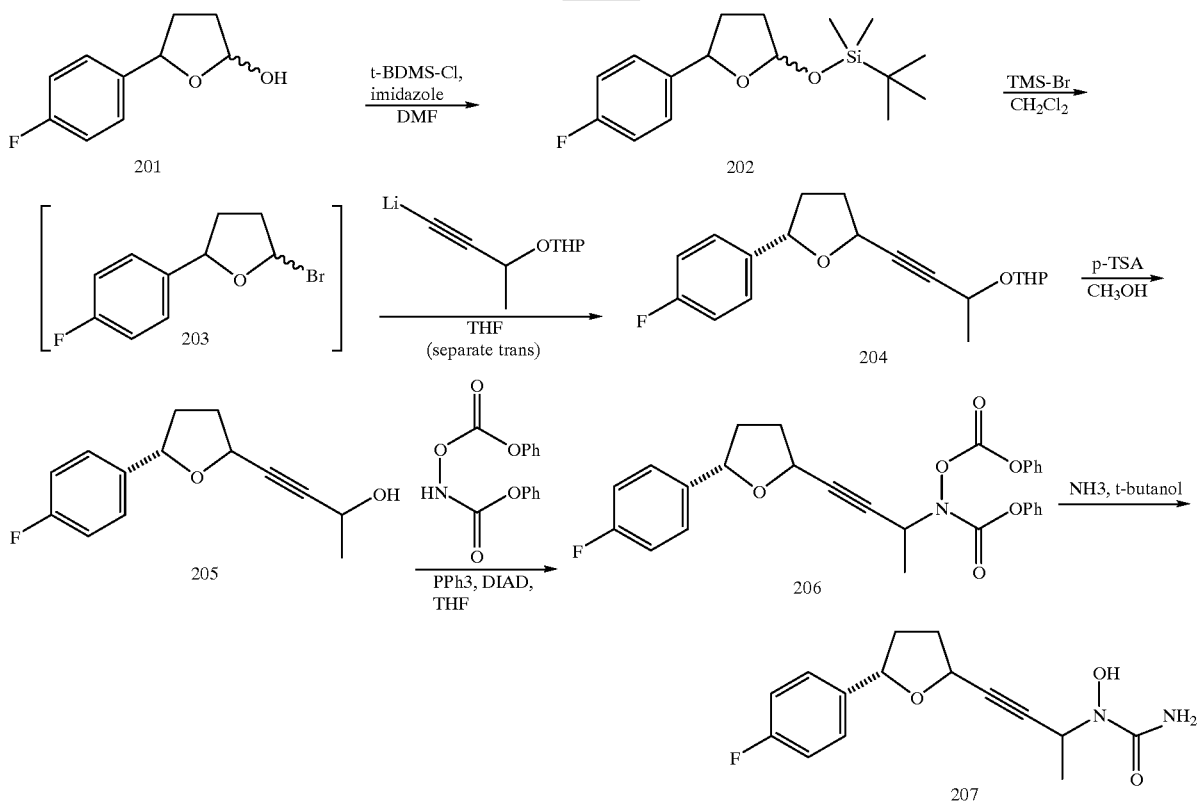

Scheme 9

(a) Preparation of 2-(t-Butyldinethylsilyloxy)-5-(4-fluorophenyl) tetrahydrofuran (compound 202):

2-Hydroxy-5-(4-fluorophenyl)-tetrahydrofuran (550 mg, 3.0 mmol), t-butyldimethylsilyl chloride (498 mg, 3.3 miol) and imidazole (450 mg, 6.6 mmol) were dissolved in 2 mL of dry DMF. This solution was stirred under dry argon overnight, poured into 200 mL of water and extracted with a 2:1 mixture of ethyl acetate( and hexane (3×100 mL). The combined organic extracts were washed with water (4×200 mL) and brine (100 mL), dried over sodium sulfate and evaporated to give 830 mg (93%) of 2-(t-butyldimethylsilyloxy)-5-(4-fluorophenyl) tetrahydrofuran (202, mixture of cis and trans isomers) as a colorless oil, which did not need any purification. $^1$H-NMR (CDCl$_3$) δ 7.40–7.50(2H, m, minor isomer), 7.25–7.35 (2H, m, major isomer), 7.00–7.10 (2H, m, both major and minor isomers), 5.71–5.75 (1H, m, major isomer), 5.59–5.62 (1H, m, minor isomer), 5.12–5.20 (1H, m, major isomer), 4.90–4.98 (1H, m, minor isomer), 2.40–2.55 (1H, m, both major and minor isomers), 2.05–2.17 (1H, m, both major and minor isomers), 1.87–2.00 (1H, m, both major and minor isomers), 1.67–1.70 (1H, m, both major and minor isomers), 0.92 (s, 9H, both major and minor isomers), 0.16 (s, 6H, both major and minor isomers).

(b) Preparation of Trans-2-(3-Tetrahydropyranyloxy-but-1-ynyl)-5-(4-fluorophenyl) tetrabydrofuran (compound 204)

2-(t-Butyldimethylsilyloxy)-5-(4-fluorophenyl) tetrahydrofuran (202, 593 mg, 2.0 mmol) was mixed in 10 mL of dry methylene chloride (degassed by bubbling argon prior to use).

This solution was cooled to −70° C. While stirring at the same temperature under dry argon, trimethylsilyl bromide (290 μL, 2.2 mol) was added dropwise. The stirring was continued for an additional 1.5 h to produce 2-bromo-5-(4-fluorophenyl) tetrahydrofuran (203) which was not isolated and was used in subsequent chemistry without further purification (see below).

In a separate flask, 3-tetrahydropyranyloxy-but-1-yne (370 mg, 2.4 mmol) was dissolved in dry THF (5 μL). The solution was cooled to −60° C. and, while stirring at the same temperature under dry argon, n-butyllithium (1.0 mL, 2.4 mmol) was added dropwise.

The stirring was continued for an additional 0.5 hours. The resulting solution was syringed out and added dropwise to the stirred solution of the 2-bromotetrahydrofuran (made above) at −70° C. The stirring was continued at −78° C. for an additional 1.5 hours. The reaction flask was stored in the freezer (−78° C.) over night (though the TLC did not show any change). The reaction mixture was poured into a 2M solution of ammonium chloride (50 mL) and extracted with methylene chloride (3×50 mL). The solution was dried over sodium sulfate and the solvent was removed in vacuo. The residue was purified via flash column chromatography (eluent, 10% ethyl acetate in hexane) to obtain two components. From the proton NMR analysis, the less polar component was identified as trans-2-(3-Tetrahydropyranyloxy-but-1-ynyl)-5-(4-fluorophenyl) tetrahydrofuran (204, 280 mg, 45%) and the more polar component (230 mg) was found to be a mixture of more than one compound. This mixture was discarded. $^1$H-NMR (CDCl$_3$) δ 7.27–7.30 (2H, m,), 7.01 (2H, t, J=8.7 Hz), 5.09 (1H, t, J=7.1 Hz), 4.91–4.95 (2H, m), 4.57–4.64 (1H, m), 3.78–3.90 (1H, m), 3.50–3.60 (1H, m),2.30–2.50 (2H, mn), 2.05–2.17 (1H, m), 1.70–1.90 (3H, m), 1.50–1.65 (4H, m), 1.48 (3H, d, J=6.6 Hz).

(c) Preparation of trans-2-(3-Hydroxy-but-1-ynyl)-5-(4-fluorophenyl) tetrahydrofuran (compoun205):

trans-2-(3-Tetrahydropyranyloxy-but-1-ynyl)-5-(4-fluorophenyl)tetrahydrofuran (204, 280 mg, 0.9 mmol) was dissolved in methanol (15 mL). To this solution was added p-toluenesulfonic acid (50 mg) and the resulting solution was stirred for 45 minutes. Saturated sodium bicarbonate solution (10 mL) was added. After 5 minutes of stirring, the solution was added to 10 mL of water, diluted with 15 mL of brine and extracted with methylene chloride (3×30 nL). The combined organics were dried over sodium sulfate and the solvent was removed via rotary evaporator to yield 212 mg (100%) of trans-2-(3-hydroxy-but-1-ynyl)-5-(4-fluorophenyl) tetrahydrofuran (205). $^1$H-NMR (CDCl$_3$) 6 7.29 (2H, dd, J=8.7, 5.2 Hz), 7.01 (2H, t, J=8.7 Hz), 5.09 (1H, t, J=7.4 Hz), 4.92 (1H, t, J=7.4 Hz), 4.59 (1H, q, J=6.6 Hz), 2.30–2.50 (2H, in), 2.05–2.15 (1H, m), 2.00 (1H, br s), 1.75–1.88 (1H, m), 1.47 (3H, d, J=6.6 Hz).

(d) Preparation of trans-2-{3-(N-Phenoxycarbonyloxy-N-phenoxycarbonyl-amino)-but-1-ynyl}-5-(4-fluorophenyl) tetrahydrofuran (compound 206):

trans-2-(3-Hydroxy-but-1-ynyl)-5-(4-fluorophenyl) tetrahydrofuran (205, 210 mg, 0.89 mmol), triphenylphosphine (288 mg, 1.1 mmol) and N,o-bis(phenoxycarbonyl) hydroxylamine (283 mg, 1.1 mmol) were dissolved in dry THF (5 mL). The solution was cooled to 0° C. under dry argon, and diisopropylazodicarboxylate (216 mL, 1.1 mmol) was added dropwise. Stirring was continued for 1 hour at the same temperature. The solvent was evaporated and the residue was purified via flash column chromatography (eluent, 30% ethyl acetate in hexane) to yield 250 mg (57%) of trans-2-{3-(N-phenoxycabonyloxy-N-phenoxycarbonyl-amino)-but-1-ynyl}-5-(4-fluorophenyl) tetrahydrofuran (206). $^1$H-NMR (CDC13) δ 7.15–7.45 (12H, m), 7.02 (2H, t, J=8.6 Hz), 5.32 (1H, q J=7.0 Hz), 5.07 (1H, t, J=6.8 Hz), 4.96 (1H, t, J=5.7 Hz), 2.25–2.50 (2H, m), 2.05–2.20 (1H, m), 1.70–1.85 (1H, m), 1.66 (3H, d, J=7.0 Hz).

(e) Preparation of trans-2-{3-(N-Kydrozyureidyl)-but-1-ynyl)-5-(4-fluorophenyl)-tetrahydrofuran (compound 207) Trans-2-{3-(N-phenoxycabonyloxy-N-phenoxycarbonyl-amino)-but-1-ynyl}-5-(4-fluorophenyl) tetrahydrofuran (206, 200 mg, 0.41 mmol) was dissolved in a high pressure tube as a solution in methylene chloride. The solvent was evaporated with a stream of argon and the residue was cooled to −78° C. Ammonia (8 mL) was condensed in this tube and 4 mL of t-butanol was added. The tube was sealed, allowed to slowly warm to the room temperature, and stirred at room temperature for 18 hours. The pressure was released very slowly and the tube was left open for 1 hour. The residue was transferred into a flask and rotavapped twice with added toluene. The residue was purified via flash column chromatography (eluent, 3% methanol in ethyl acetate) and was further purified on a preparative TLC (solvent, 5% methanol in methylene chloride) to give 93 mg (78%) of Trans-2-{3-(N-hydroxyureidyl)-but-1-ynyl}-5-(4-fluorophenyl) tetrahydrofuran (207). IR (film) 3481, 3269, 2985, 2877, 2249, 1662, 1670, 1510, 1444, 1224, 1172, 1037 cm$^{-1}$; $^1$H-NMR (CDCl$_3$) 6 8.10 (1H, br s), 7.2(3 (2H, dd, J=8.6, 5.4 Hz), 7.00 (2H, t, J=8.6 Hz), 5.80 (1H, br s), 5.00–5.20 (2H, m), 4.80–5.00 (1H, m), 2.20–2.50 (2H, m), 2.00–2.20 (1H, m), 1.70–1.90 (1H, m), 1.37 (3H, dd, J=6.9, 1.9 Hz).

EXAMPLE 5

Preparation of S,S,S- and S,S,R-isomers of trans-2-{3-(N-Hydroxyureidyl)-but-1-ynyl}-5-(4-fluorophenyl)-tetrahydrofuran (compounds 216 and 217)

One method for the preparation of the S,S,R- and S,S,S-isomers of trans-2-{3-(N-Hydroxyureidyl)-but-1-ynyl}-5-(4-fluorophenyl)-tetrahydrofuran is illustrated below in Scheme 10.

Scheme 10
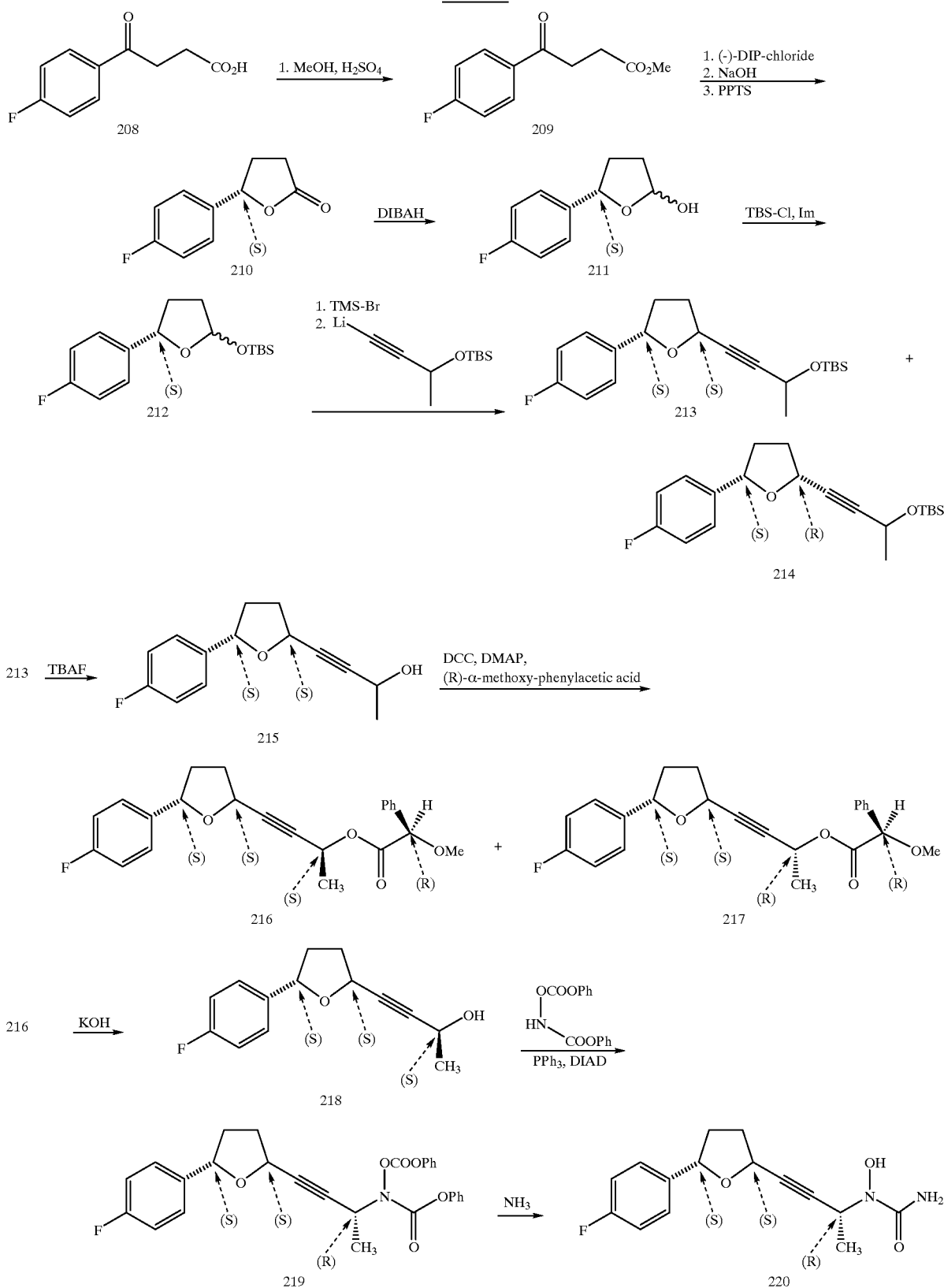

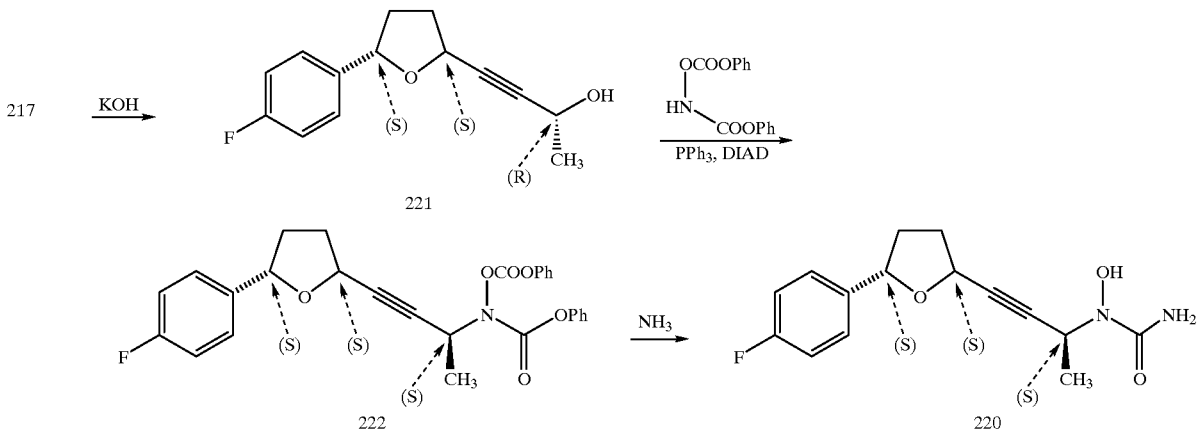

(a) Preparation of Methyl 3-(4-fluorobenzoyl)-propionate (compound 209)

To a solution of 3-(4-fluorobenzoyl)-propionic acid (1.98 g, 10.0 =ol) in methanol (25 mL) was added 0.5 mL of conc. sulfuric acid. The resulting solution was stirred at room temperature under argon for 2 hours. The reaction mixture was neutralized with saturated sodium bicarbonate, the methanol was removed via rotary evaporator and the residue was dissolved in 50 mL of ethyl acetate. The resulting solution was washed with saturated sodium bicarbonate (3×50 nL) and brine (50 -mL), dried over sodium sulfate and the solvent was removed in vacuo to give Methyl 3-(4-fluorobenzoyl)-propionate (2 g, 94%). IR (film) 3448, 3111, 3076, 3003, 3958, 1734, 1678, 1601, 1423, 1300, 1240, 1155, 1099 cm$^{-1}$; $^1$H-NMR (CDCl$_3$) δ 7.97 (2H, dd, J=9.0, 5.5 Hz), 7.10 (2H, t, J=8.9 Hz), 3.67 (3H, s), 3.25 (2H, t, J=6.6 Hz), 2.73 (2H, t, J=6.6 Hz); $^{13}$C-NMR (CDCl$_3$) δ 196.50, 173.34, 167.54, 164.17, 132.98, 130.77, 115.91, 115.62, 51.91, 33.31, 28.00.

(b) Preparation of (S)-5-(4-fluorophenyl)-γ-butyrolactone (compound 210)

A solution of methyl 3-(4-fluorobenzoyl)-propionate (209, 780 mg, 3.67 mmol) in dry THF (2 mL) was added, dropwise, to a precooled (0° C.) solution of (−)-DIP-chloride (2.02 g, 6.25 mmol) in THF (2 mL) with stirring under dry argon. The resulting solution was stirred at the same temperature for 2 hours and allowed to stand at 0–5° C. overnight. Maintaining the temperature at 0° C., with stirring, water (2 mL) was added dropwise, followed by methanol (5 mL) and a 5 M NaOH solution (5 mL). The reaction mixture was stirred at room temperature for 1.5 hours, cooled, and 15 mL of saturated-bicarbonate solution was added. The resulting mixture was washed with ether (3×50 mL) and acidified with 6 N HCl. The acidic mixture was extracted with toluene (3×50 mL). The combined toluene extracts were washed with brine (50 mL), dried over sodium sulfate and the solvent was removed in vacuo. The residue was resuspended in 50 mL of toluene and PPTS to (10 mg) was added to it. The resulting solution was refluxed under a Dean-Stark trap (first 15 mL of the distillate were drained off) for 2 hours. The solution was cooled, washed with saturated bicarbonate solution (2×50 mL), dried over sodium sulfate and the solvent was removed in vacuo to yield 620 mg (94%) of (S)-5-(4-fluorophenyl)-γ-butyrolactone. $^1$H-NMR (CDCl$_3$) δ 7.33 (2H, dd, J=8.8, 5.3 Hz), 7.09 (2H, t, J=8.7 Hz), 5.50 (1H, dd, J=8.4, 5.9 Hz), 2.64–2.71 (3H, m), 2.17–2.22 (1H, m).

(c) Preparation of (58)-2-Hydroxy-S-(4-fluorophenyl) tetrahydrofuran (compound 211)

(S)-5-(4-Fluorophenyl)-7-butyrolactone (210, 620 mg, 3.44 mmol) was dried azeotropically (with hexane) and dissolved in d.y. methylene chloride (25 mL). The solution was cooled to −78° C. and, with stirring under argon, DIBAH (3.5 mL of 1.5 M solution in toluene, 5.16 mmol) was added dropwise. Stirring was continued at −78° C. for 2 hours and then a saturated solution of Na-K-tartarate (25 mL) was added. The cooling bath was removed and the stirring was continued for additional 2 hours. The reaction mixture was diluted with methylene chloride (25 mL). The organic layer was separated, washed with water (2×50 mL) and brine (50 mL), dried over sodium sulfate and the solvent was removed in vacuo to yield 2-hydroxy-5-(4-fluorophenyl) tetrahydrofuran (620 mg, 100%). $^1$H-NMR (CDCl$_3$) 6 7.30–7.41 (m, 2H), 7.04 (m, 2H), 5.63–5.78 (m, 1H), 5.00–5.22 (m, 1H), 2.48 (m, 1H), 2.20–2.32 (m,1H), 1.95–2.10 (m, 1H), 1.79 (m, 1H).

(d) Preparation of (58)-2-(t-Butyldinothylsilyloxy)-5-(4-fluorophenyl) tetrahydrofuran (compound 212):

(5S)-2-Hydroxy-5-(4-fluorophenyl) tetrahydrofuran (211, 620 mg, 3.5 mmol), t-butyldimethylsilyl chloride (700 mg, 5.25 mmol) and imidazole (595 mg, 8.75 mmol) were dissolved in 2 mL of dry DMF. The resulting solution was stirred under dry argon overnight, poured into 200 mL of water, and extracted with a 2:1-mixture of ethyl acetate and hexane (3×100 mL). The combined organic extracts were washed with water (4×200 mL) and brine (100 mL), dried over sodium sulfate and the solvent was removed in vacuo to yield 1 g (96%) of (5S)-2-(t-Butyldimethylsilyloxy)-5-(4-fluorophenyl) tetrahydrofuran (212, mixture of cis and trains isomers) as a colorless oil, which did not need further purification. $^1$H-NMR (CDCl$_3$) δ 7.40–7.50(2H, m, minor isomer), 7.25–7.35 (2H, m, major isomer), 7.00–7.10 (2H, m, both major and minor isomers), 5.71–5.75 (1H, m, major isomer), 5.59–5.62 (1H, m, minor isomer), 5.12–5.20 (1H, m, major isomer), 4.90–4.98 (1H, m, minor isomer), 2.40–2.55 (1H, m, both major and minor isomers), 2.05–2.17 (1H, m, both major and minor isomers), 1.87–2.00 (1H, m, both major and minor isomers), 1.67–1.70 (1H, m, both major and minor isomers), 0.92 (s, 9H, both major and minor isomers), 0.16 (s, 6H, both major and minor isomers).

(e) Preparation of (22,58)-trans-2-(3-t-butyldinethylsilyloxy-but-1-ynyl)-5-(4-fluorophenyl) tetrahydrofuran (compound 213):

(5S)-2-(t-Butyldimethylsilyloxy)-5-(4-fluorophenyl) tetrahydrofuran (212, 1 g, 3.4 mmol) was dissolved in 10 mL of dry methylene chloride (degassed by bubbling argon prior to use). This solution was cooled to −70° C. and, while stirring at the same temperature under dry argon, trimethylsilyl bromide (550 μL, 4.1 mmol) was added dropwise. The stirring was continued for an additional 1.5 hours to yield (5S)-2-bromo-5-(4-fluorophenyl) tetrahydrofuran which was used without isolation (see below). In a separate flask, 3-t-butyldimethylsilyloxy-but-1-yne (840 mg, 4.5 mmol) was dissolved in dry THF (10 mL). The solution was cooled to −60° C. and, while stirring at the same temperature under dry argon, n-butyllithium (1.8 mL of 2.5M solution in hexane, 4.5 mmol) was added dropwise. The stirring was continued for an additional 0.5 hours. The resulting solution was added dropwise, through a cannula to the stirred solution of the 2-bromotetrahydrofuran (made above) at −70° C. The stirring was continued at −78° C. for additional 1.5 hours. The reaction flask was then left in the freezer (−78° C.) over night (though the TLC did not show any change). The reaction mixture was poured into 2M solution of ammonium chloride (100 mL) and extracted with methylene chloride (3×75 mL). The solution was dried over sodium sulfate and the solvent removed in vacuo. The residue was purified via flash column chromatography (eluent, 10% ethyl acetate in hexane) to obtain two components. From the proton NMR analysis, the less polar one was identified as (2S,5S)-trans-2-(3-t-butyldimethylsilyloxy-but-1-ynyl)-5-(4-fluorophenyl) tetrahydrofuran (213, 765 mg, 65%). $^1$H-NNR (CDCl$_3$) δ 7.29 (2H, m), 7.01 (2H, t, J=8.7 Hz), 5.09 ($^1$H, t, J=7.1 Hz), 4.91–4.97 (2H, m), 4.55–4.62 (1H, m), 2.26–2.50 (2H, m), 2.05–2.17 (1H, m), 1.75–1.88 (1H, m), 1.38 (3H, d, J=6.6 Hz), 0.90 (9H,s), 0.12 (6H, s). The more polar component was assigned to be (2R,5S)-cis-2-(3-t-butyldimethylsilyloxy-but-1-ynyl)-5-(4-fluorophenyl) tetrahydrofuran (214, 190 mg, 16%).

(f) Preparation of (2S,5S)-trans-2-(3-hydroxy-but-1-ynyl)-5-(4-fluorophenyl) tetrahydrofuran (compound 215):

(2S,5S)-trans-2-(3-t-butyldimethylsilyloxy-but-1-ynyl)-5-(4-fluorophenyl) tetrahydrofuran (213, 765 mg, 2.2 mmol) was dissolved in 20 mL of THF. The solution was cooled to 0° C. and TBAF (6.6 mL of 1M solution in THF) was added to it. The resulting solution was stirred at 0° C. for 2h and the solvent was removed in vacuo. The residue was dissolved in ethyl acetate (100 mL), washed with water (3×100 mL, added 5 mL of brine each time to separate layers) followed by brine (50 mL), dried over sodium sulfate and the solvent removed in vacuo to yield 500 mg (97%) of (2S,5S)-trans-2-(3-hydroxy-but-1-ynyl)-5-(4-fluorophenyl) tetrahydrofuran (215). $^1$H-NMR (CDCl$_3$) δ 7.29 (2H, dd, J=8.7, 5.2 Hz), 7.01 (2H, t, J=8.7 Hz), 5.09 (1H, t, J=7.4 Hz), 4.92 (1H, t, J=7.4 Hz), 4.59 (1H, q, J=6.6 Hz), 2.30–2.50 (2H, m), 2.05–2.15 (1H, m), 1.75–1.88 (1H, m), 1.72 (1H, br s), 1.47 (3H, d, J=6.6 Hz).

(2S,5S)-trans-2-(3-Hydroxy-but-1-ynyl)-5-(4-fluorophenyl) tetrahydrofuran (215, 500 mg, 2.13 mmol), (R)-a-Methoxy-phenylacetic acid (1.06 g, 6.4 mmol) and DMAP (86 mg, 0.7 mmol) were dissolved in dry methylene chloride (3 mL)). DCC (1.5 g, 7.24 mmol) was added and the resulting solution was stirred at room temperature, under dry argon, for 3h (a lot of white solid precipitated within minutes). The solid was filtered off and the filtrate was concentrated in vacuo. The residue was purified vi[]a flash column chromatography (eluent, 8% ethyl acetate in hexane) to obtain the two diastereomeric esters. The less polar one wa.,3 assigned to be from (2S,5S)-trans-2-{3-(S)-hydroxy-but-1-ynyl}-!5-(4-fluorophenyl) tetrahydrofuran (216, 250 mg, 30%, >95% de from $^1$H-NMR). $^1$H-NMR (CDCl$_3$) δ 7.25–7.50 (7H, m), 7.02 (2H, t, J=8.5 Hz), 5.52–5.60 (1H, m), 5.06 (1H, t, J=6.8 Hz), 4.88–4.94 (1H, m), 4.78 (1H, s), 3.43 (3H, s), 2.25–2.47 (2H, m), 2.00–2.13 (IR, m), 1.75–1.88 (1H, m), 1.37 (3H, d, J=6.7 Hz). The more polar one was assigned to be from (2S,5S)-trans-2-{3-(R)-hydroxy-but-1-ynyl}-5-(4-fluorophenyl) tetrahydrofuran (217, 230 mg, 29%, 72% de from $^1$H-NMR). $^1$H-NMR (CDCl$_3$) δ 7.22–7.50 (7H, m), 7.01 (2H, t, J=8.7 Hz), 5.50–5.60 (1H, m), 4.98 (1H, t, J=7.2 Hz), 4.79–4.85 (1H, m), 4.79 (1H, s), 3.44 (3H, s), 2.20–2.40 (2H, m), 1.88–1.98 (1H, m), 1.72–1.80 (1H, m), 1.51 (3H, d, J=6.7 Hz). Basic hydrolyses (stirring in 10 mL of 1M ethanolic KOH at 50° C. for 30 min followed by usual workup) of these two esters gave their respective alcohols; (2S,5S)-trans-2-{3-(S)-hydroxy-but-1-ynyl}-5-(4-fluorophenyl) tetrahydrofuran (218, 150 mg, 98%) and its diastereomer (2S,5S)-trans-2-{3-(R)-hydroxy-but-1-ynyl}-5-(4-fluorophenyl) tetrahydrofuran (221, 50 mg, 100%). The $^1$H-NMR 34 spectra for both these alcohols were identical to that of 218.

(g) Preparation of (2S,5S)-trans-2-{3-(R)-(N-phrnoxycarbonyloxy-M-phenoxycarbonyl-amino)-but-1-ynyl}-5- (4-fluorophenyl) tetrahydrofuran (compound 219):

(2S,5S)-trans-2-{3-(S)-hydroxy-but-1-ynyl}-5-(4-fluorophenyl) tetrahydrofuran (218, 150 mg, 0.64 immol), triphenylphosphine (200 mg, 0.77 mmol) and N,O-bis (phenoxycarbonyl)hydroxylanine (200 mg, 0.77 anol) were dissolved in dry THF (3 mL). The solution was cooled to 0° C. and with stirring under dry argon was added diisopropylazodicarboxylate (142 μL, 0.77 mmol) dropwise. The stirring was continued for 1 h at the same temperature. The solvent was evaporated on a rotavap and the residue was purified via flash column chromatography (eluent, 30% ethyl acetate in hexane) to give 225 mg (72%) of (2S,5S)-trans-2-{3-(R)-(N-phenoxycabonyloxy-N-phenoxycarbonyl-amino)-but-1-ynyl}-5-(4-fluorophenyl) tetrahydrofuran (219). $^1$H-NMR (CDCl$_3$) δ 7.15–7.45 (12H, m), 7.02 (2H, t, J=8.6 Hz), 5.32 (1H, q J=7.0 Hz), 5.07 (1H, t, J=6.8 Hz), 4.96 (1H, t, J=5.7 Hz), 2.25–2.50 (2H, m), 2.05–2.20 (1H, m), 1.70–1.85 ($^1$H, m), 1.66 (3H, d, J=7.0 Hz).

(h) Preparation of (2S,5S)-trans-2-{3-(8)-(N-phenozycabonyloxy-N-phenoxycarbonyl-amino)-but-1-ynyl}-5-(4-fluorophenyl) tetrahydrofuran (cu pound 222):

Starting with (2S,5S)-trans-2-{3-(R)-hydroxy-but-1-ynyl}-5-(4-fluorophenyl) tetrahydrofuran (221, 150 mg, 0.64 mmol), following the same procedure for 218, 220 mg (70%) of (2S,5S)-trans-2-{3-(S)-(N-phenoxycabonyloxy-N-phenoxycarbonyl-amino)-but-1-ynyl}-5-(4-fluorophenyl) tetrahydrofuran (222) was obtained. The $^1$H-NMR was identical to that of 219.

(i) Preparation of (2S,5S)-trans-2-{3-(R)-(N-hydroxyureidyl)-but-1-ynyl}-5-(4-fluorophenyl) tetrahydrofuran (compound 220):

(2S,5S)-trans-2-{3-(R)-(N-phenoxycabonyloxy-N-phenoxycarbonyl-amino)-but-1-ynyl}-5-(4-fluorophenyl) tetrahydrofuran (219, 225 mg) was dissolved in a high pressure tube as a solution in inethylene chloride. The solvent was evaporated with a stream of argon and the residue was cooled to −78° C. 10 mL of ammonia was condensed in this tube and 2 mL of t-butanol was added. The tube was sealed and was allowed to slowly warm to the room temperature. Then it was left stirring at roomi temperature for 18 hours. The pressure was released very slowly and the tube was left open for 1 hour. The residue was transferred into a flask and concentrated under vacuum twice with added toluene. The residue was purified via preparative TLC (eluent, 5% methanol in methylene chloride) to give 120 mg (90%) of (2S,5S)-trans-2-13-(R)-(N-hydroxyureidyl)-but-1-ynyl}-5-(4-fluorophenyl) tetrahydrofuran (220). IR (film)

3209, 2985, 2874, 1653, 1510, 1449, 1336, 1224, 1157, 1037 cm$^{-1}$; $^{1}$H-NMR (CD$_3$OD) δ 7.34 (2H, dd, J=8.7, 5.4 Hz), 7.04 (2H, t, J=8.8 Hz), 5.00–5.10 (2H, m), 4.85–4.95 (1H, m), 2.25–2.50 (2H, m), 2.00–2.15 (1H, m), 1.78–1.85 (1H, m), 1.38 (3H, d, J=7.0 Hz).

(j) Preparation of (2S,5)-trans-2-{3-(8)-(N-hydroxyureidyl)-but-1-ynyl}-5-(4-fluorophenyl) tetrahydrofuran (compound 223):

Starting with (2S,5S)-trans-2-{3-(S)-(N-phenoxycabonyloxy-N-phenoxycarbonyl-amino)-but-1-ynyl}-5-(4-fluorophenyl) tetrahydrofuran (222, 225 mg), following the same procedure for 219, 110 mg (83%) of (2S,5S)-trans-2-{3-(S)-(N-hydroxyureidyl)-but-1-ynyl}-5-(4-fluorophenyl) tetrahydrofuran (223) was obtained. IR (film) 3200, 2985, 2881, 1643, 1510, 1442, 1222, 1035 cm$^{-1}$; $^{1}$H-NMR (CD$_3$OD) g 7.34 (2H, dd, J=8.7, 5.5 Hz), 7.04 (2H, t, J=8.9 Hz), 5.00–5.10 (2H, m), 4.85–4.95 (1H, m), 2.25–2.50 (2H, m), 2.00–2.15 (1H, m), 1.70–1.85 (1H, m), 1.38 (3H, d, J=7.0 Hz).

EXAMPLE 6

Preparation of R,R,S- and R,R,R-isomers of trans-2-{3-(N-Hydroxyureidyl)-but-1-ynyl}-5-(4-fluorophenyl)-tetrahydrofuran (compounds 234 and 236) One method for the preparation of the S,S,R- and S,S,S-isomuers of trans-2-{3-(N-Hydroxyureidyl)-but-1-ynyl}-5-(4-fluorophenyl)-tetrahydrofuran is illustrated below in Scheme 11.

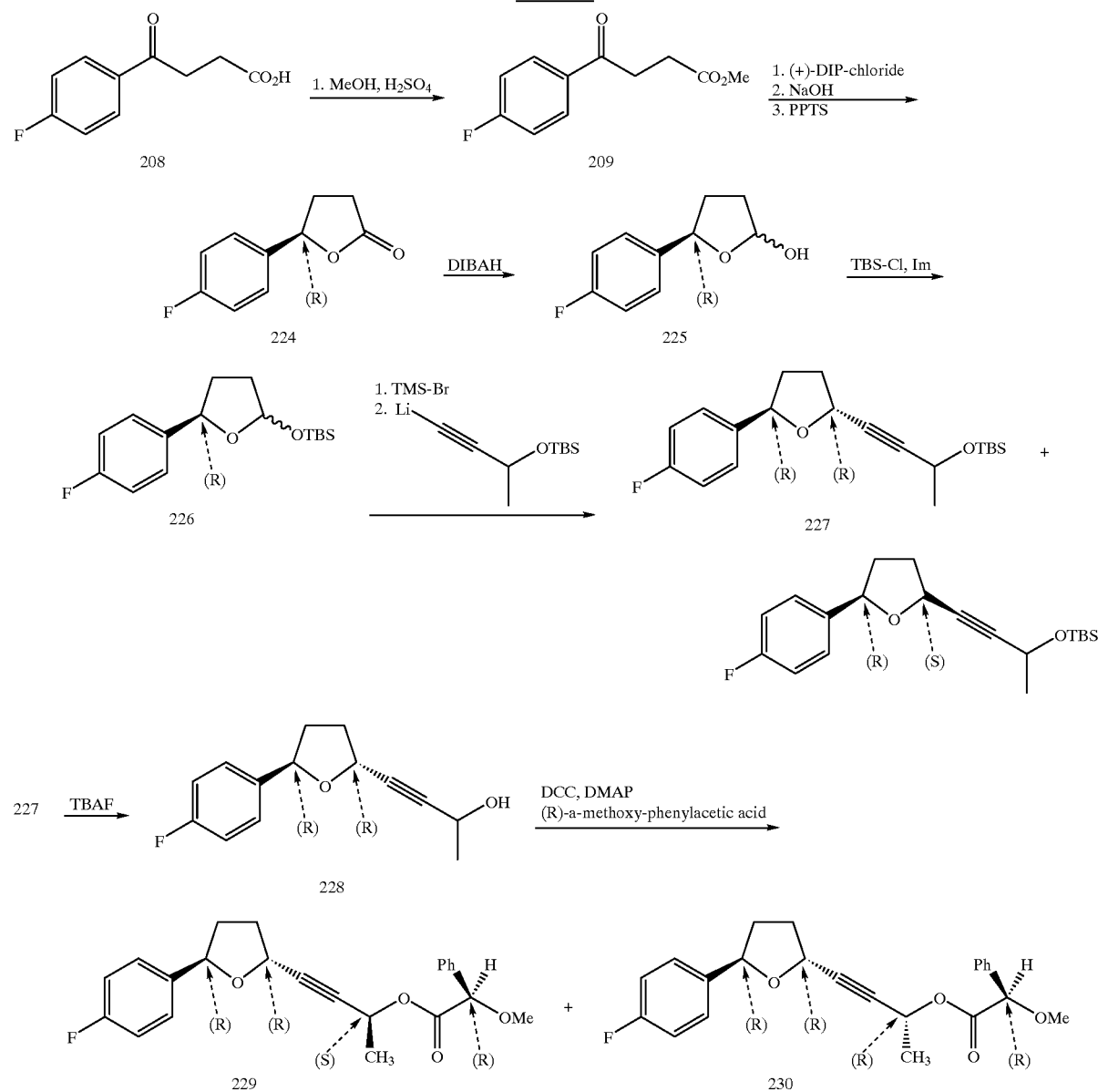

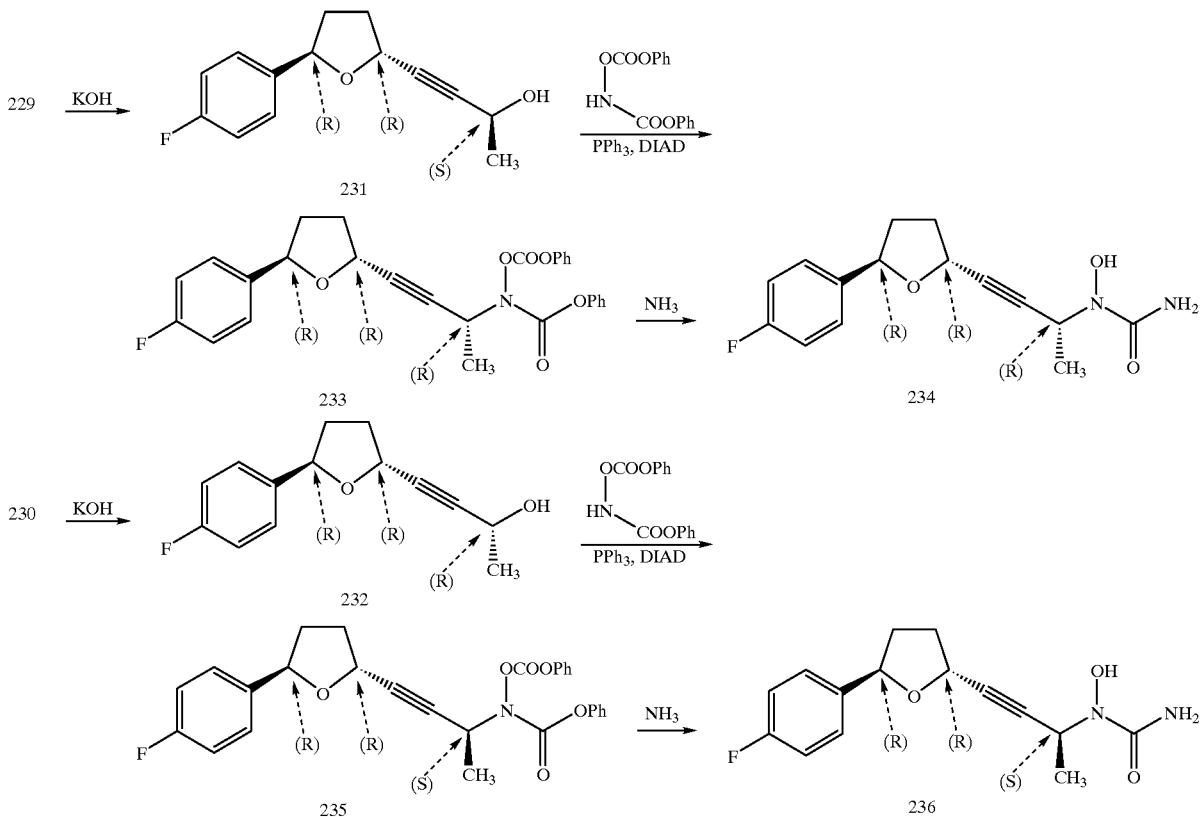

(a) Preparation of 4-(4-fluorophenyl)-4-oxo-methylbutanoate (compound 209)

To a stirred solution of 3-(4-benzoyl)propionic acid (208) (5.0 g) in methanol (20 mL) was added a few drops of sulfuric acid. After stirring overnight (19 hrs) the reaction was neutralized with saturated aqueous sodium bicarbonate and the methanol was removed under reduced pressure. The residue was dissolved in ethyl acetate (50 mL) and washed with saturated aq. sodium bicarbonate (3×15 mL), water (2×15 mL), and brine (2×15 mL), dried ($Na_2SO_4$), filtered and concentrated to give a pale crystalline solid (5.3 g, 98%). $^1$H NMR: 2.79(t, 2H), 3.30(T, 2H), 3.71(S, 3H), 7.14(T, 2H), 8.02(m,2H).

(b) Preparation of R-4-(4-fluorophenyl)-gamma-butyrolactone (compound 224)

To a cooled (0° C.), stirred solution of (+)-DIP chloride (25 g, 77.9 mmol) in dry THF (20 mL) under argon was slowly added a solution of the keto-ester 209 (10.07 g, 48.0 mmol) in dry THF (20 mL). The reaction was placed in a refrigerator (4° C.) for 30 hours, and then was returned to an ice bath and stirred while water (10 mL), then methanol (30 mL), then 10% NaOH(, (60 mL) were added. The ice bath was removed. When all of the ester had been hydrolized, saturated aq. sodium bicarbonate (80 mL) was added. The aqueous was extracted with ether (2×100 mL), then acidified to pH 2 and extracted with benzene (2×180 mL).

Pyridinium-p-toluenesulfonate (60 mg) was added to the combined benzene layers which were then heated to reflux using a Dean-Stark trap. When the reaction was complete the benzene solution was washed with saturated aq. sodium bicarbonate (150 mL) and brine (2×50 mL), dried ($Na_2SO_4$), filtered and concentrated to give. a white crystalline solid which was assigned the R configuration based on literature precedent (7.92 g, 91%). $^1$H NMR 2.10–2.25(m, 1H), 2.68 (m, 3H), 5.50(m, 1H), 7.08(t, 2H), 7.30(m, 2H).

(c) Preparation of Cis and trans-SR-S-(4-fluorophenyl)-2-hydroxy tetrabydrofuran (compound 225):

To a stirred solution of the lactone 224 (7.25 g, 40.3 mmol) in dry toluene (50 mL), cooled in a dry ice/acetone bath was added diisobutylaluminum hydride (1.5M in toluene)(1.5eq., 40 mL). When the reaction was complete, methanol (10 mL) was slowly added, then saturated ag. sodium potassium-L-tartrate (60 mL) and the ice bath was removed. This solution was stored overnight (16 hours), the layers were separated and the aqueous fraction extracted with ethyl acetate (2×50 mL). The combined organic layers were washed with water (3×30 mL) and brine (3×30 mL), dried ($Na_2SO_4$), filtered and concentrated. The product was a colorless oil which was a mixture of two diastereomers (ca. 50/50) (6.32 g, 86%).

1H NMR: 1.7(m, 1H), 1.9–2.3(m, 2H), 2.42(m, 1H), 3.60(bs, 0.5H), 3.72(bs, 0.5H), 4.98(t, 0.5H), 5.20(t, 0.5H), 5.60(bs, 0.5H), 5.72(m, 0.5H), 7.00(t, 2H), 7.25(m, 1H), 7.40(m, 1H).

(d) Preparation of cis and trans-5R-5-(4-fluorophenyl)-2-t-butyldinethylsiloxy tetrabydrofuran (compound 226):

To a stirred solution of the lactol 225 (6.32 g, 34.7 mmol) in methylene chloride (140 mL) was added imidazole (1.1 eq, 38.2 mmol, 2.60 grams) and TBDMS chloride (5.77 grams). After stirring overnight the reaction was filtered and concentrated. The crude product was filtered through a plug of silica to give a colorless oil which is a mixture of two diastereomers (ca. 2:1) (9.61 g, 93%).

$^1$H NM: 0.14(s, 6H), 0.92(s, 9H), 1.7(m, 1H), 1.9–2.2(m, 2H), 2.4–2.5(m, 1H), 4.9(m, 0.33H), 5.16(t, 0.66H), 5.59(m, 0.33H), Mt 5.71(dd, 0.66H), 7.00(m, 2H), 7.25(m, 1.33H)i 7.40(m, 0.66H).

For a sample of this compound with a racemic mixture and the 5 position, the presence of each configuration at this center war, detectable using a chiral solvating agent [2,2,2-trifluoro-1-(9-anthryl)ethanol, 2.2 mg substrate, 40 mg CSA]. These condition showed that compound 226 had no detectable amount of the 5S isomer.

For the control, a 2:1 diastereomeric mixture of compound 226 (2.2 mg) in which the 5 position was a racemic mixture was treated with the CSA (40 mg). The multiplet at 4.86–4.92 ppm (0.33H) became two multiplets at 4.64–4.72 and 4.78–4.84 ppm. For the other diastereomer (same spectrum) the doublet of doublets at 5.66–5.70 ppm became two sets of dd's at 5.64–5.68 and at 5.70–5.74 ppm. For the chirally reduced compound, the smaller multiplet (w/CSA) appears at 4.62–4.70 and the doublet of doublets appears at 5.68–5.70 ppm. No evidence of the other isomers was seen.

(e) Preparation of 2R,5R-trans-S-(4-fluorophenyl)-2-(3-t-butyldinethylsiloxy-1-butynyl)tetrahydrofuran (compound 227):

To a solution of 226 (500 mg, 1.69 mmol) in dry degassed methylene chloride (10 ml), cooled to −78° C. was added TMS bromide (0.25 mL, 1.86 mmol). This was stirred for four hours. In a separate flask containing 3-t-butyldimethylsiloxy-1-butyne (0.31 g, 1.68 mmol) and THF(5 mL) was added n-butyllithium (1.6M in hexanes, 1.26 mL, 2.02 mmol). After 30 minutes, the solution was transferred by cannula to the solution from above. After two hours the reaction was poured into 2M aq. ammonium chloride (25 mL) and extracted into methylene chloride (3×25 mL), dried ($Na_2SO_4$), filtered and concentrated. Flash chromatography (5% ethyl acetate in hexanes) gave ther trans product as a clear oil (280 mg, 48%).

$^1$H NMR: 0.17(d, 6H), 0.91(s, 9H), 1.42(d, 3H), 1.8(m, 1H), 2.25–2.50(m, 2H), 4.58(m, lH), 4.91(m, 1H) 5.09(m, 1H), 7.0(t, 2H), 7.30(m, 2H).

(f) Preparation of 2R, 5R-trans-5-(4-Fluorophenyl)-2-(3-hydroxy-1-butynyl)tetrahydrofuran (compound 228):

To a stirred solution of 227 (0.38 g, 1.1 mmol) in THF (5 mL) cooled in an ice bath was added tetrabutyl ammonium fluoride (0.86 g, 3.3 mmol). The ice bath was removed. After 30 minutes the solvent was removed and the products were separated by flash chromatography (25% ethyl acetate in hexanes). The product was a colorless oil (170 mg, 67%). $^1$H NMR: 1.48(d, 3H), 1.8(m, 1H), 2.1(m, 1H), 2.3–2.5(m, 2H), 4.58(m, 1H), 4.91(t, 1H), 5.1(t, 1H), 7.0(t, 2H), 7.29(m, 2H).

The hydroxy function of 228 was esterified with R-alpha-methoxyphenylacetic acid (DCC, DMAP, $CH_2Cl_2$, 55% after chromatography) and the resulting diastereomers (229+230) were separated (flash chromatography), thus isolating the R and S isomers at the carbinol carbon. The ester was removed by base hydrolysis (KOH, 78%)to give the carbinols 231 and 232. Absolute configurations were assigned based on the Mosher model.

(g) Preparation of 2R, 5R-trans-5-(4-fluorophenyl)-2-(3R-3-N,O-bisphenozycorbonyl hydroxylamino-1-butynyl)tetrahydrofuran (compound 233)

To a cooled (ice bath) solution of 2R,5R-trans-5-((4-fluorophenyl)-2-(3S-3-hydroxy-1-butynyl)tetrahydrofuran (231) (29) mg, 0.12 mmol), triphenylphosphine (39 mg, 0.15 mmol) and N,O-bisphenoxycarbonyl hydroxylamine (37 mg, 0.14 mmol) in THF (3 mL) was slowly added diisopropylazodicarboxylate (0.029 mL, 0.15 mmol). The ice bath was removed and when the reaction was complete (a few minutes) the solvent was removed. The product was obtained by flash chromatography (15% ethyl acetate in hexanes) as a colorless oil (32 mg, 53%).

$^1$H NMR: 1.65(d, 3H), 1.8(m, 1H), 2.1(m, 1H), 2.4(m, 2H), 4.94(m, 1H), 5.08(m, 1H), 5.30(m, $^1$H), 7.0(t, 2H), 7.15–7.40(m, 2H).

(h) Preparation of 2R, 5R-trans-5-(fluorophenyl)-2-(3R-3-N-hydroxyureidyl-1-butynyl)tetrahydrofuran (compound 234):

Compound 233 (32 mg) was combined in a screw cap vessel at −78° C. with a stir bar, condensed ammonia (ca. 3 mL) and t-butanol (ca. 2 mL). The-vessel was sealed and the cold bath removed. After stirring overnight at room temperature the pressure was released and the solvent was removed. The product was triturated (25% ethyl acetate in hexanes) to give a white solid (14 mg, 74%). $^1$H NMR: 1.41(d, 3H), 1.8(m, 1H), 2.1(m, 1H), 2.3–2.5(m, 2H), 4.93(t, 1H), 5.08(t, 1H), 5.20(m, 1H), 5.38(bs, 1H), 7.0(t, 2H), 7.29(m, 2H). Electrospray MS: M+1=293.

The synthesis of the RRS isomer (compound 236) proceeds in if the same fashion from the ester 230 as did the RRR isomer (234) from ester 229.

II. Pharmaceutical Compositions

Humans, equines, canines, bovines and other animals, and in, particular, mammals, suffering from inflammatory diseases, and in particular, disorders mediated by PAF or products of 5-lipoxygenase can be treated by administering to the patient an effective amount of one or more of the above-identified compounds or a pharmaceutically acceptable derivative or salt thereof in a pharmaceutically acceptable carrier or diluent to reduce formation of oxygen radicals. The active materials can be administered by any appropriate route, for example, orally, parenterally, intravenously, intradermally, subcutaneously, or topically, in liquid, cream, gel, or solid form, or by aerosol form.

As used herein, the term pharmaceutically acceptable salts or complexes refers to salts or complexes that retain the desired biological activity of the above-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. The compounds can also be administered as pharmaceutically acceptable quaternary salts known by those skilled in the art, which specifically include the quaternary ammonium salt of the formula -NR+Z- , wherein R is alkyl or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 10 ng/kg to 300 mg/kg, preferably 0.1 to 100 mg/kg per day, more generally 0.5 to about 25 mg per kilogram body weight of the recipient per day. A preferred dosage for cardiovascular indications is in the range 10 ng/kg tc 20 mg/kg. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient is preferably administered to achieve peak plasma concentrations of the active compound of about 0.00001–30 nm, preferably about 0.1–30 $\mu$M. This may be achieved, for example, by the intravenous injection of a solution or formulation of the active ingredient, optionally in saline, or an aqueous medium or administered as a bolus of the active ingredient. The concentration of active compound in the drug composition will depend on absorption, distribution, inactivation, and excretion rates of the drug as well as other factors known to those of skill in the art. It is to be noted that dosage values will also vary with the severity of the condition to be be alleviated. It is to be further understood that for any particular subject, specific dosage regimens should be adjusted over time according to the individual need and the professional judgment of the person administering or supervising the administration of the compositions, and that the concentration ii ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsule. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, other antiinf lammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Scios Nova (Baltimore, Md.).

Liposonal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin 11 film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have been used to evaluate the ability of a compound to act as a PAF receptor antagonist, including the ability of the compound to bind to PAF receptors, and the effect of the compound on various PAF mediated pathways. Any of these known assays can be used to evaluate the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse.

Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can result in severe shock and death. Endotoxin-induced mouse mortality is a useful animal model to evaluate the pharmacological effect of compounds on endotoxic shock.

Two other common assays used to evaluate the ability of a compound to act as a PAF receptor antagonist are platelet aggregation in vitro and hypotension in rats (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987)).

A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by inhibition of $LTB_4$ from ionophore stimulated human whole blood.

EXAMPLE 5
Ability of Compound to Bind to PAP Receptors (a) Preparation of Human Platelet Kembranes Human platelet membranes are prepared from platelet concentrates obtained from the American Red Cross Blood Services (Dedham, Mass.). After several washes with platelet wash solution (150 mM NaCl, 10 mM Tris, and 2 mM EDTA, pH 7.5), the platelet pellets are resuspended in 5 mM $MgCl_2$, 10 mM Tris, and 2 mM EDTA at pH 7.0. The cells are then quickly frozen with liquid nitrogen and thawed slowly at room temperature. The freezing and. thawing procedure is repeated at least three times. For further fractionation of membrane fragments, the lysed membrane suspension is layered over the top of a discontinuous sucrose density gradient of 0.25, 1.03, and 1.5 M sucrose prepared in 10 MM $MgCl_2$, 10 mM Tris and 2 mM EDTA, pH 7.0, and centrifuged at 63,500×g for 2 hr. The membrane fractions banding between 0.25 and 1.03 M (membrane A) and between 1.03 and 1.5 M (membrane B) are collected separately. The protein concentration of the membrane preparations is determined by Lowry's method with bovine serum albumin (BSA) as the standard. The membranes are then separated into smaller fractions (4 ml each) and stored at −80° C. and thawed before use.

(b) [$^3$H]PAY Binding inhibition

The ability of [3H]PAF to bind tb specific receptors on human platelet membranes is evaluated at optimal conditions at pH 7.0 and in the presence of 10 nM $MgCl_2$. Membrane protein (100 µg) is added to a final 0.5 ml solution containing 0.15 pmol (0.3 nM concentration) of [3H]PAF and a known amount of unlabeled PAF or PAF receptor antagonist in 10 mM $MgCl_2$, 10 mM Tris and 0.25% BSA at pH 7.0. After incubation for four hours at 0° C., the bound and unbound [$^3$H]PAF are separated through a Whatman GF/C glass fiber filter under vacuum. No degradation of filter bound [$^3$H]PAF should be detected under this assay condition. The An5 nonspecific binding is defined as the total binding in the presence of excess unlabeled PAF (1 mM) where no further displacement is found with higher concentrations of either unlabeled PAF or PAF analogs or PAF receptor antagonists. The specific binding is defined as the difference between total binding and nonspecific binding.

To determine the relative potency of tested compounds, [3H]PAF binding in the presence of inhibitors is normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition=[(Total binding−total binding in the presence of comp6und)/nonspecific binding]×100%

The $IC_5$ is calculated as the concentration of the inhibitor necessary to obtain 50% inhibition of the specific [$^3$H]PAF binding and is calculated by a nonlinear regression computer software program, GraphPad Inplot, version 3.0 (GraphPad. software, San Diego, Calif.).

EXAMPLE 6
Effect of Coupound on VAP-induced Hemoconcentration (a) Animals

Female CD-1 mice, weighing 16–20 grams, are obtained from Charles River Laboratory (Wilmington, Mass.). Tap water and rodent laboratory chow (5001, Purina Mills, St. Louis, Mont.) are provided ad libitum. The mice are housed for an average of four days prior to use.

(b) Hematocrit measurement

PAF (1-O-alkyl-2-acetyl-sn-glyceryl-3-phosphorylcholine, Sigma Chemical Co.) is dissolved in 0.25% bovine serum albumin (BSA) in 0.9% NaCl solution. Except for dose-response studies, 10 µg (10 ml/kg) of PAF solution is injected into the tail vein.

All test compounds are dissolved in 0.5 DMSO saline solution and intravenously injected at 3 mg/kg body weight 15 minutes prior qto PAF challenge. Thirty to fifty lL blood is collected by cuttinig the tail end into a heparinized micro-hematocrit tube (O.D. 1.50 mm) 15 minutes after PAF administration. All test compounds are given intravenously at 3 mg/kg 15 minutes before PAF (10 ug/kg, intravenously) or AA (0.5 mg/ear) in mice.

EXAMPLE 7
Effect of Compounds on Cytosol 5-Lipoxygenase of Rat Basophile Leukemia Cells (a) Enzyme preparation Washed rat RBL cells (4×108) were suspended in 20 ml of 50 M potassium phosphate buffer at pH 7.4 containing 10% ethylene glycol/1 mM EDTA (Buffer A). The cell suspension was sonicated at 20 KHz for 30 seconds, and the sonicate was centrifuged at 10,000×g for 10 minutes, followed by further centrifugation at 105,000×g for 1 hr. The supernatant solution (cytosol fraction) containing 5-lipoxygenase was stored at −70° C. Protein concentration was determined according to the procedure of Bradford (Bradford Dye Reagent) with bovine serum albumin as a standard.

(b) Enzyme assay

For routine assay of 5-lipoxygenase the mixture contained 50 nM potassium phosphate buffer at pH 7.4, 2 mM $CaCl_2$, 2 mM ATP, 25 M arachidonic acid (0.1 Ci) and enzyme (50–100 mg of protein) in a final volume of 200 L. The reaction was carried out at 24° C. for 3 minutes. The mixture was extracted with 0.2 ml of an ice-cold mixture of ethyl ether:methanol: 0.2 M citric acid (30:4:1).

The extract was subjected to thin-layer chromatography at −10° C. in a solvent system of petroleum ether:ethyl ether::acetic acid (15:85:0.1). The silica gel zones corresponding to authentic arachidonic acid and its metabolites were scraped into scintillation vials for counting. The enzyme activity was expressed in terms of the amount of arachidonic acid oxygenated for 3 minutes. Representative compounds 9, 11, 14, and 15, identified above, showed activity in this assay.

Table 3 provides data for the inhibition of soluble 5-lipoxygenase in RBL-1 cell extract by racemic compound 202, as 1-M well as its enantiomers, compounds 220, 223, 234, and 236.

EXAMPLE 8
Inhibition of Loukotriene BE Production in Ionophors-stimulated human whole blood Human blood is drawn into heparinized blood collection tubes, and aliquoted in 1 ml portions into 1.5 ml microfuge tubes. Five milliliters of test compound at varying concentrations, dissolved in DMSO, is added to the blood sample and incubated for 15 minutes at 37° C. Calcium ionophore (5 ml) (A23187) in DMSO is added to a final concentration of 50 mM, and the samples are incubated for 30 minutes at 37° C. Samples are then centrifuged at 1100×g (2500 rpm, H1000B rotor, in a Sorvall centrifuge) for 10 minutes at 4° C. 100 ml of supernatant is transferred into a 1.5 ml microfuge tube, 400 ml of cold methanol is added, and proteins are precipitated on ice for 30 minutes. The samples are centrifuged at 110×g for 10 minutes at 4° C., and the supernatant is assayed for $LTB_4$ using a commercially available EIA kit (Cayman Chemical) according to manufacturer's specifications.

Table 3 provides data for the inhibition of leukotriene $B_4$ production in Ionophore-stimulated human whole blood by racemic compound 202, as well as its enantiomers, compounds 216, 217, 234, and 236.

EXAMPLE 9
EX-vivo mouse and rat wvole blood 5-lipoxygenase evaluation

CD-1 female mice, weighing 18–25 grams, and CD female rates, weighing 150–230 grams, were obtained from Charles River Labs. _Compounds were dissolved in 0.5% DMSO in 0.9% NaCl for administration in mice (0.5 mg/ml) and in an alcohol vehicle (2% benzyl alcohol, 1% ethanol, 40% PEG 300 10% propylene glycol, 471 of 5% dextrose plus 3.5% pluronic F-68 in $DiH_2O$) for use in rates (5 mg/ml). Animals were injected with compound (5 mg/kg) or corresponding vehicle (0.5% DMSO in saline, 10 ml/kg for mice; alcohol vehicle, 1. ml/kg for rats) 15 minutes before they were sacrificed by decapitation. Heparinized whole blood (0.3 ml) was added into 1.5 ml Eppendorf centrifuge tub containing 3 ml of 2 mM calcium ionophore A23187 (the final concentration of A23187 was 20 mM). The sample was incubated for 30 minutes in a water bath of 37° C., and then centrifuged for 2 minutes. The plasma was diluted (x120) and assayed for $LTB_4$ using EIA.

Table 3 provides data for the ex-vivo mouse and rat whole blood 5-lipoxygenase values on administration of racemic compound 202, as well as its enantiomers, compounds 216, 217, 234, and 236.

EXAMPLE 10
Rate of Glucuronidation

The rate of glucuronidation is a measure of the metabolic stability in vivo of the compounds disclosed herein.

In vitro glucuronidation reactions were carried out with reaction mixtures containing 2 mg/ml of human microsomal protein, 5 mM magnesium chloride, 100 mM Tris HCl (pH=7.4), 0.1–1.0 MM substrate and 3 mM UDP-glucuronic acid. After incubation at 37° C. for 0 (control), 15, 30, 45, 60, 90, 120, 180, 240 minutes, 40 µl aliquots of the reaction mixture were mixed with 80 µl of acetonitrile and centrifuged to remove the precipitated protein. Aliquots of the supernatant were analyzed by reverse phase HPLC nS to determine the disappearance of parent compounds and formation of metabolites.

Figure 2:
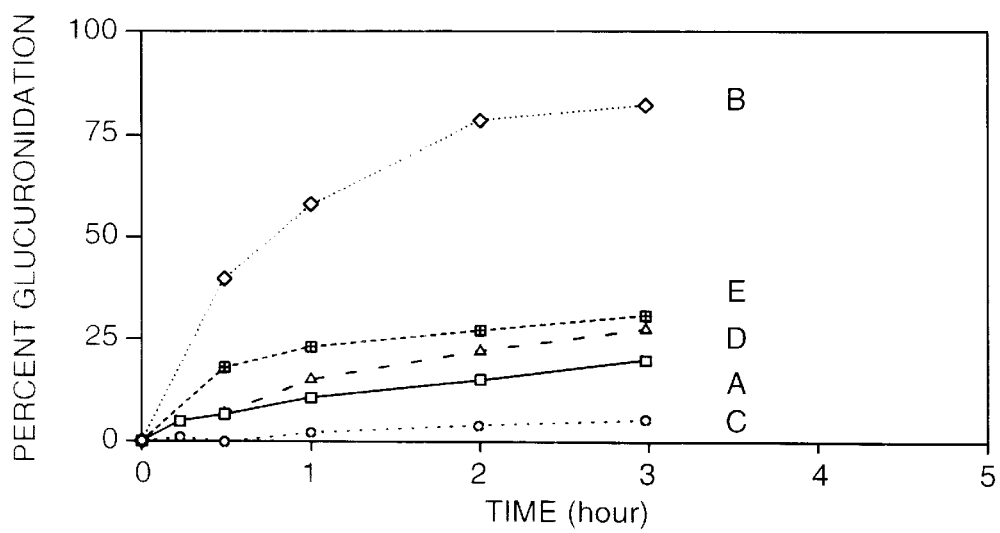
FIG. 2 illustrates the rate of glucuronidation of racemic compound 202, as well as its enantiomers, compounds 216, 217, 234, and 236.
Figure 2:
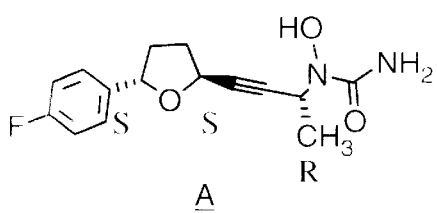
Figure 2:
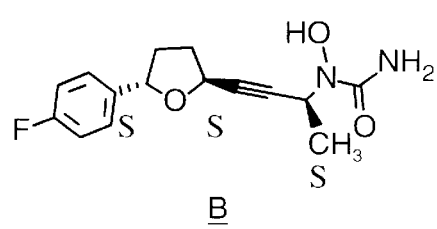
Figure 2:
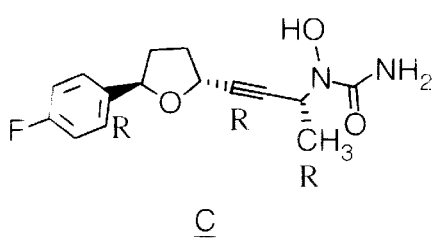
Figure 2:
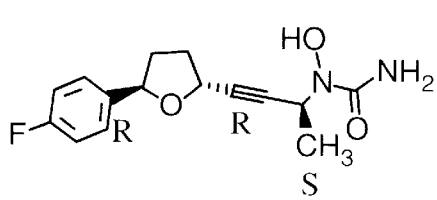
Figure 2:
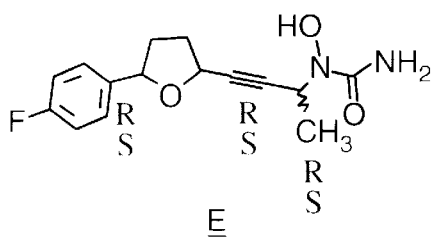

Table 3 provides data for, and FIG. 2 illustrates, the rate of glucuronidation of racemic compound 202, as well as its enantiomers, compounds 216, 217, 234, and 236.

Figure 3:
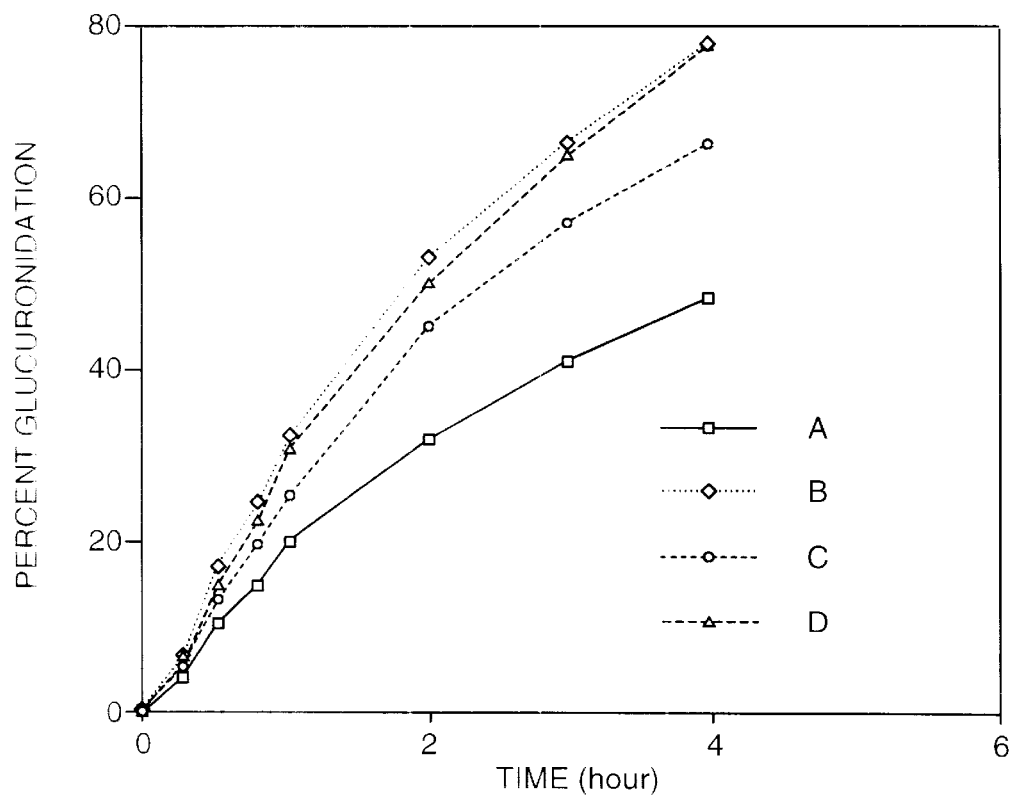
FIG. 3 illustrates the rate of glucuronidation for the following illustrated enantiomers.
Figure 3:
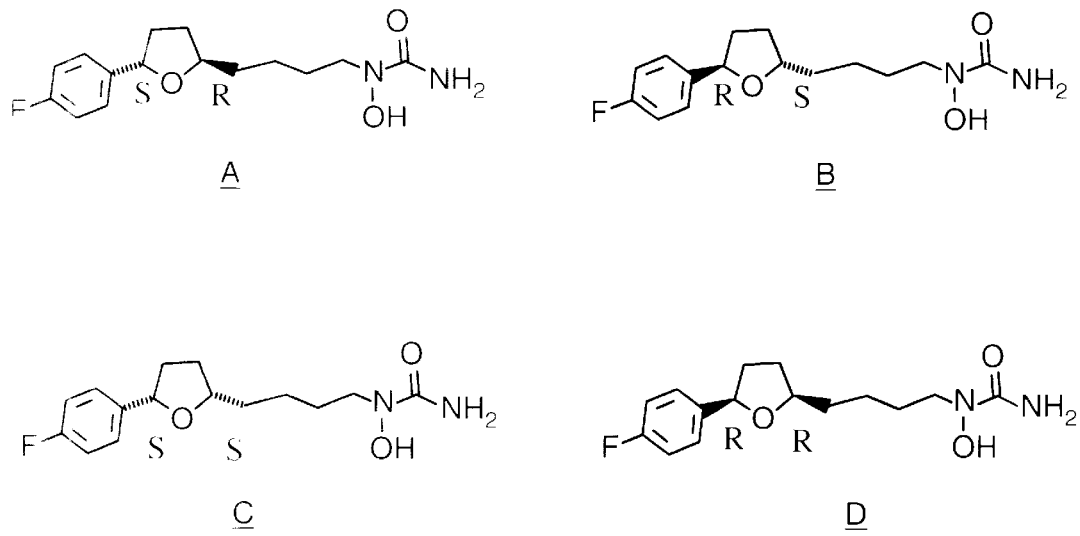

FIG. 3 illustrates the rate of glucuronidation for illustrated enantiomers.

Modifications and variations of the present invention relating to compounds that reduce the formation of oxygen radicals during an inflammatory or immune response will be obvious to those skilled in the art from the foregoing detailed description of the invention. Such modifications and variations are intended to come within the scope of the appended claims.

TABLE 3

| STRUCTURE | RBL | | | HWB | | | ex vivo LTB4 | | |
|---|---|---|---|---|---|---|---|---|---|
| | dose uM | % inh. | IC50 nM | dose uM | % inh. | IC50 | dose mg/k | % inh. | IC50 |
| 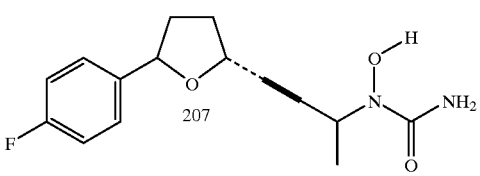 207 | 1.6 | 20 | 2800 | | | 0.48 | 5, po<br>5, po<br>2, po<br>2, po | | RAT<br>96, 60'<br>96, 180'<br>43, 60'<br>38, 360' |
| 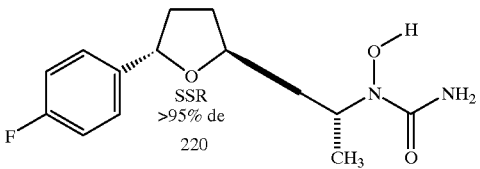 220 SSR >95% de | | | 3800 | | | 0.76 | 2, po<br>2, po<br>2, po | | RAT<br>88, 60'<br>57, 160'<br>38, 360' |

TABLE 3-continued

| STRUCTURE | RBL dose uM | RBL % inh. | RBL IC50 nM | HWB dose uM | HWB % inh. | HWB IC50 | ex vivo LTB4 dose mg/k | ex vivo LTB4 % inh. | ex vivo LTB4 IC50 |
|---|---|---|---|---|---|---|---|---|---|
| 223 SSR 72% de (4-F-phenyl-tetrahydrofuran-CH(CH3)-N(OH)-C(O)-NH2) | | | 3500 | | | 0.22 | | | |
| 234 RRR >95% de | | | 3100 | | | 3.2 | 2, po / 2, po / 2, po / 2, po | RAT 40, 60'; 52, 180'; 46, 160'; 12, 360' | |
| | | | | | | | 2, po / 2, po / 2, po | RAT 73, 60'; 65, 180'; 28, 360' | |
| 236 RRS >95% de | | | 2000 | | | 0.75 | 2, po / 2, po / 2, po / 2, po | RAT 42, 60'; -4, 180'; -5.6, 60'; -1, 180' | |
| (4-F-phenyl-THF-(CH2)4-N(OH)-C(O)-NH2) | | | 618 | | | .230 | 3, iv / 3, iv / 10, po / 10, po | RAT 97, 60'; 22, 120'; 81.8, 60'; 83., 180' | |
| S,R TRANS | | | 1100 | | | 0.097 | 2, po / 2, po / 2, po / 2, po | RAT 81, 60'; 7.2, 180'; 63, 60'; 37, 180' | |
| R,S TRANS | | | | | | 0.143 | | | |
| S,S CIS | | | | | | 0.145 | | | |
| R,R CIS | | | | | | 0.173 | | | |

We claim:
1. An enantiomerically enriched compound of formula:

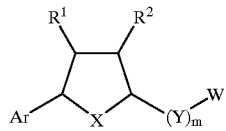

(I)

wherein:
- Ar is an aryl or heteroaryl group that is optionally substituted with at least one group selected from the group consisting of halo, lower alkoxy, lower aryloxy, W, cyano, or $R^3$;
- m is 0 or 1;
- W is independently $-AN(OM)C(O)N(R^3)R^4$, $-AN(R^3)C(O)N(OM)R^4$, $-AN(OM)C(O)R^4$, $-AC(O)N(OM)R^4$, $-C(O)N(OM)^4$, $-C(O)NHA$, $-A-B$;
- A is lower alkyl, lower alkenyl, lower alkynyl, alkaryl or aralkyl groups, wherein one or more carbons optionally can be replaced by O, N, or S;
- B is selected from the group consisting of pyridylimidazole and benzimidazole, either of which is optionally substituted with $R_3$;
- M is hydrogen, a pharmaceutically acceptable cation, or a metabolically cleavable leaving group;
- X is O, S, S(O), $NR^5$, or $CHR^5$;
- Y is O, S, S(O), $NR^5$, or $CHR^5$;
- $R^1$ and $R^2$ are independently hydrogen, lower alkyl; halo lower alkyl; halo; and $-COOH$;
- $R^3$ and $R^4$ are independently hydrogen or alkyl, alkenyl, alkynyl, aryl, aralkyl, alkaryl, $C_{1-6}$ alkoxy-$C_{1-10}$ alkyl, $C_{1-6}$ alkylthio-$C_{1-10}$ alkyl, heteroaryl, or heteroarylalkyl-;
- $R^5$ is hydrogen, lower alkyl, lower alkenyl, lower alkynyl, alkaryl, $-AN(OM)C(O)N(R^3)R^4$, $-AN(R^3)C(O)N(OM)R^4$, $-AN(OM)C(O)R^4$, $-AC(O)N(OM)R^4$, $-AC(O)N(OM)R^4$, $-AS(O)nR^3$, $-AS(O)_nCH_2C(O)R^3$, $-AS(O)_nCH_2CH(OH)R^3$, $-AC(O)NHR^3$; and wherein n is 0–2.

2. The compound of claim 1, wherein Ar is selected form the. group consisting of phenyl, trimethoxyphenyl, dimethoxyphenyl, fluorophenyl, and specifically 4-fluorophenyl, difluorophenyl, pyridyl, dimethoxypyridyl, quinolinyl, furyl, imidazolyl, and thienyl.

3. The compound of claim 1, wherein $-A-B$ is

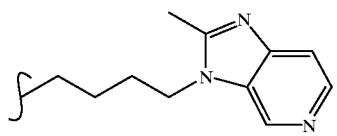

and wherein Ar is aryl or heteroaryl substituted with at least one group selected from W, halo, hydroxyl, amino, alkylamino, arylamino, alkoxy, aryloxy, nitro, cyano, sulfonic acid, sulfate, phosphonic acid, phosphate, and phosphonate.

4. The compound of claim 1, wherein Ar is selected from 4-fluorophenyl, 3,4,5-methoxyphenyl, 3,4-dimethoxyphenyl, 5-(2,3-dimethoxypyridyl), 3,4-difluorophenyl, 3-quinolinyl and

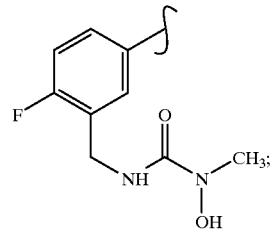

X is selected from O, $CH_2$, S and NH;
Y is selected from O, $CH_2$, S, NH and direct link;
$R^1$ and $R^2$ are hydrogen; and
W is selected from $-CH_2CH_2CH_2NHC(O)N(OH)CH_3$, $-CH_2CH_2CH_2NHC(O)N(OH)CH_2CH_2CH_2CH_3$, $-CH_2CCHH_2N(OH)C(O)NH_2$, $-CH_2CH_2CH_2N(OH)C(O)NHCH_3$, $-CH_2CH=CHCH_2N(OH)CONH_2$, $-C\equiv CCH_2N(OH)C(O)NH_2$, $-C\equiv CCH(CH_3)N(OH)C(O)NH_2$, $-CH_2CH_2CH_2CH_2N(OH)C(O)NH_2$, and

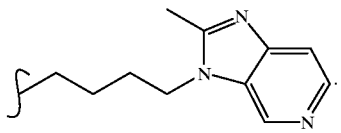

5. An enantiomerically enriched compound selected from the group consisting of: 2-(3,4,5-trimethoxyphenyl)-5-[3-(N'-methyl-N'-hydroxyureidyl)propoxy] tetrahydrofuran;
  2-(4-fluorophenyl)-5-[3-(N'-methyl-N'-hydroxyureidyl) propoxy]tetrahydrofuran;
  2-(3,4,5-trimethoxyphenyl)-5-[3-(N'-n-butyl-N'-hydroxyureidyl)-propoxy]tetrahydrofuran;
  2-(4-fluorophenyl)-5-[3-(N'-n-butyl-N'-hydroxyureidyl) propoxy] tetrahydrofuran;
  2-(3',4'-dimethoxyphenyl)-5-[3-(N-butyl-N-hydroxyureidyl)]-propoxytetrahydrofuran;
  2-(3',4'-dimethoxyphenyl)-5-[3-(N-methyl-N-hydroxyureidyl)]-propoxytetrahydrofuran;
  2-(2,4,5-trimethoxyphenyl)-5-(3-hydroxyureidylpropoxy)-tetrahydrofuran;
  2-(4-fluorophenyl)-5-(3-hydroxyureidyl-propoxy) tetrahydrofuran;
  2-(4-fluorophenyl)-5-[3-(N'-methyl-N'-hydroxyureidyl) propoxy]tetrahydrothiophene; and
  2-(4-fluorophenyl)-5-(3-hydroxyureidyl-propoxy) tetrahydrothiophene.

6. A pharmaceutical composition comprising an effective amount of the compound of claim 1, 2, 3, 4, or 5 or a pharmaceutically acceptable salt thereof, and a pharmaceutically acceptable carrier.

7. A method for the treatment of inflammatory disorders in a host comprising administering an effective amount of a compound of claim 1, 2, 3, 4, or 5 or a pharmaceutically acceptable salt thereof.

8. A method for the treatment of a patient in need of immunosuppression comprising administering an effective amount of the compound of claim 1, 2, 3, 4, or 5 or a pharmaceutically acceptable salt thereof.

9. The method of claim 7, wherein the animal is selected from a human, a mammal, an equine, a canine and a bovine.

10. The method of claim 8, wherein the animal is selected from a human, a mammal, an equine, a canine and a bovine.

11. A method for the treatment of a cardiovascular disorder comprising administering an effective amount of the compound of claim 1, 2, 3, 4, 5, or a pharmaceutically acceptable salt thereof.

12. A method for the inhibition of 5-lipoxygenase in a patient comprising administering an effective amount of the compound of claim 1, 2, 3, 4, 5, or a pharmaceutically acceptable salt thereof.

13. A compound selected from the group consisting of

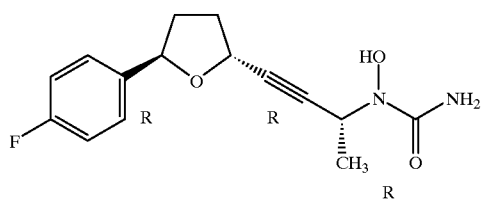
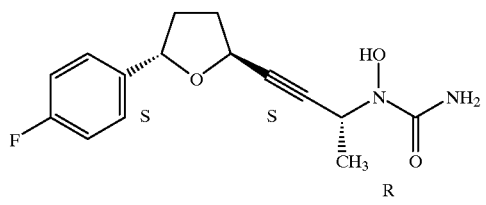
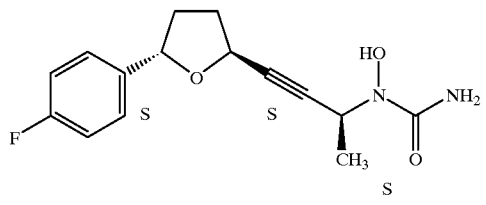
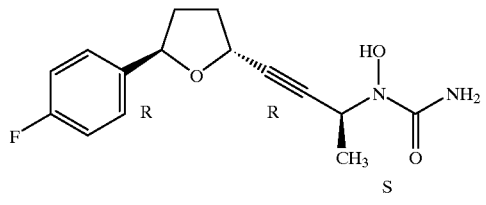
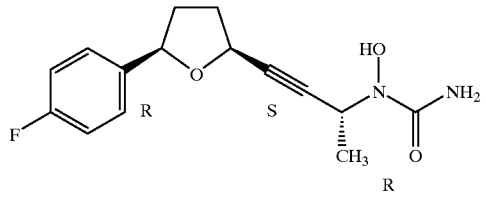
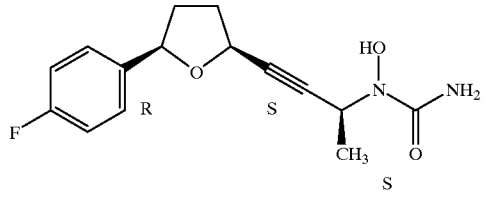
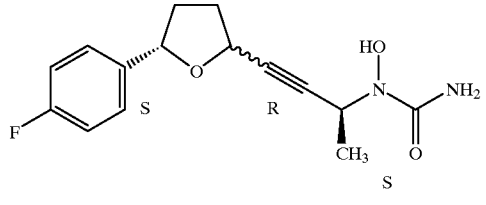
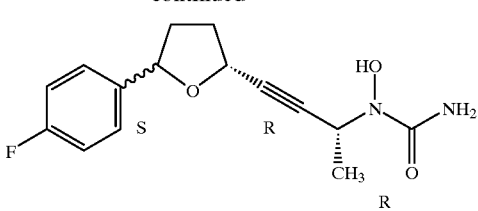
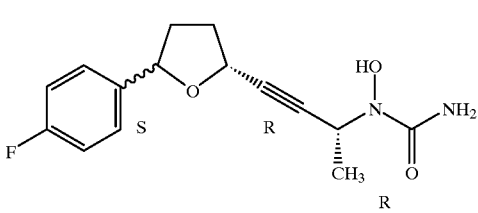
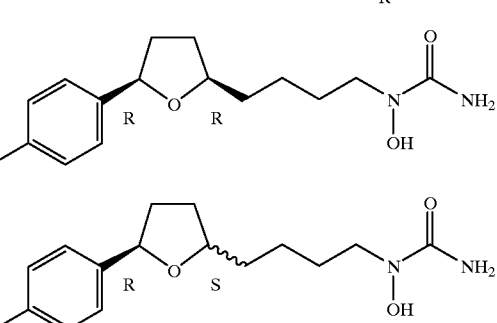
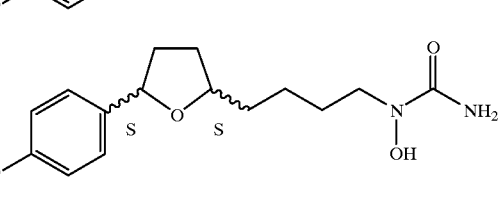
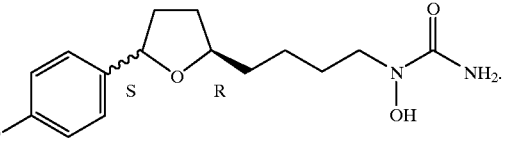

14. A compound selected from the group consisting of:

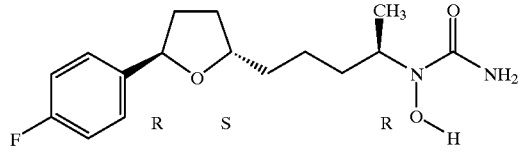
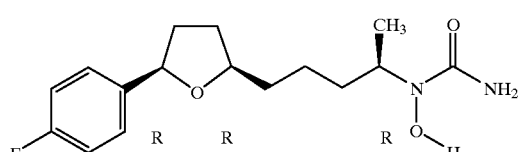
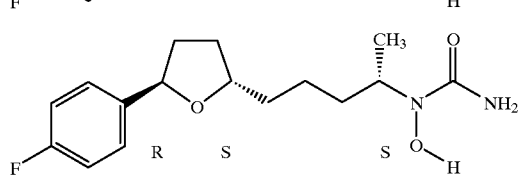

-continued
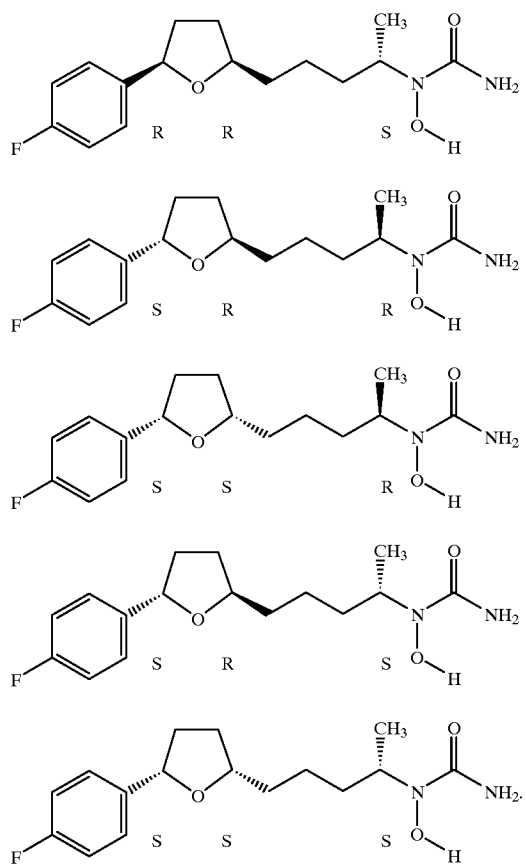
15. A compound selected from the group consisting of:
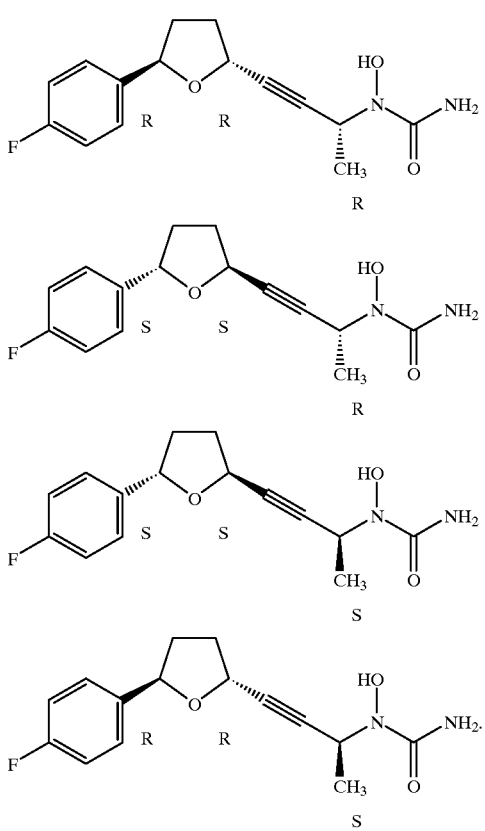
* * * * *